(12) United States Patent
Chandrasekaran et al.

(10) Patent No.: US 9,649,824 B2
(45) Date of Patent: *May 16, 2017

(54) LAMINATES INCLUDING A RETICULATED THERMOPLASTIC FILM AND METHOD OF MAKING THE SAME

(71) Applicant: 3M INNOVATIVE PROPERTIES COMPANY, St. Paul, MN (US)

(72) Inventors: Neelakandan Chandrasekaran, Woodbury, MN (US); Thomas P. Hanschen, Mendota Heights, MN (US); Timothy P. Pariseau, Forest Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 492 days.

This patent is subject to a terminal disclaimer.

(21) Appl. No.: 13/901,043

(22) Filed: May 23, 2013

(65) Prior Publication Data
US 2014/0349079 A1 Nov. 27, 2014

(51) Int. Cl.
*B32B 3/24* (2006.01)
*B32B 3/26* (2006.01)
(Continued)

(52) U.S. Cl.
CPC .......... *B32B 3/263* (2013.01); *A44B 18/0015* (2013.01); *A44B 18/0049* (2013.01);
(Continued)

(58) Field of Classification Search
CPC .................. Y10T 428/24306; B32B 3/263
See application file for complete search history.

(56) References Cited

U.S. PATENT DOCUMENTS

| 3,012,275 A | 12/1961 | Nalle, Jr. |
| 3,054,148 A | 9/1962 | Zimmerli |

(Continued)

FOREIGN PATENT DOCUMENTS

| EP | 0191355 | 8/1986 |
| EP | 1641417 | 4/2006 |

(Continued)

OTHER PUBLICATIONS

U.S. Application entitled, "Mechanical Closure Element", filed Aug. 16, 2012, having U.S. Appl. No. 29/429,801.

(Continued)

*Primary Examiner* — William P Watkins, III

(57) ABSTRACT

A laminate of an at least partially reticulated thermoplastic film joined to an extensible carrier. The reticulated thermoplastic film includes a backing with openings and discrete elements protruding from the first major surface. There are two discrete elements aligned in a first direction abutting opposite ends of any given opening. In a second direction perpendicular to the first direction, there is one discrete element between the given opening and an adjacent opening aligned in the second direction. Each portion of the thermoplastic backing around the given opening is plastically deformed in its lengthwise direction. A method of making a laminate is also disclosed. The method includes stretching a thermoplastic backing having a plurality of discrete elements in the first direction and laminating the backing to an extensible carrier. Subsequently stretching the laminate in a second direction forms a tear in the thermoplastic backing between two adjacent of the discrete elements.

18 Claims, 7 Drawing Sheets

200 μm

(51) Int. Cl.
*A44B 18/00* (2006.01)
*B32B 38/00* (2006.01)
*B32B 37/14* (2006.01)
*B32B 5/02* (2006.01)
*B32B 5/26* (2006.01)
*B32B 27/12* (2006.01)
*B32B 27/30* (2006.01)
*B32B 27/32* (2006.01)
*B32B 27/34* (2006.01)
*B32B 27/40* (2006.01)
*B32B 7/12* (2006.01)
*B32B 3/30* (2006.01)
*A61F 13/62* (2006.01)
*A61F 13/60* (2006.01)
*A61F 13/15* (2006.01)

(52) U.S. Cl.
CPC ........ *A61F 13/15756* (2013.01); *A61F 13/60* (2013.01); *A61F 13/622* (2013.01); *A61F 13/625* (2013.01); *B32B 3/266* (2013.01); *B32B 3/30* (2013.01); *B32B 5/02* (2013.01); *B32B 5/022* (2013.01); *B32B 5/26* (2013.01); *B32B 7/12* (2013.01); *B32B 27/12* (2013.01); *B32B 27/306* (2013.01); *B32B 27/32* (2013.01); *B32B 27/34* (2013.01); *B32B 27/40* (2013.01); *B32B 37/144* (2013.01); *B32B 38/0012* (2013.01); *B32B 2038/0028* (2013.01); *B32B 2262/0253* (2013.01); *B32B 2262/0261* (2013.01); *B32B 2262/0276* (2013.01); *B32B 2274/00* (2013.01); *B32B 2305/38* (2013.01); *B32B 2307/51* (2013.01); *B32B 2307/726* (2013.01); *B32B 2555/02* (2013.01); *Y10T 24/27* (2015.01); *Y10T 428/24306* (2015.01); *Y10T 428/24504* (2015.01)

(56) References Cited

U.S. PATENT DOCUMENTS

| | | | |
|---|---|---|---|
| 3,178,328 A | | 4/1965 | Tittmann |
| 3,252,181 A | | 5/1966 | Hureau |
| 3,302,501 A | | 2/1967 | Greene |
| 3,394,211 A | | 7/1968 | MacDuff |
| 3,471,597 A | | 10/1969 | Schirmer |
| 3,616,154 A | * | 10/1971 | Dow et al. .................. 428/134 |
| 3,717,908 A | | 2/1973 | Perina |
| 3,831,741 A | | 8/1974 | Poupitch |
| 3,985,599 A | | 10/1976 | Lepoutre |
| 3,985,600 A | | 10/1976 | Blais |
| 4,001,366 A | | 1/1977 | Brumlik |
| 4,038,008 A | | 7/1977 | Larsen |
| 4,087,226 A | | 5/1978 | Mercer |
| 4,152,479 A | | 5/1979 | Larsen |
| 4,384,022 A | | 5/1983 | Fowler |
| 4,435,141 A | | 3/1984 | Weisner |
| 4,472,328 A | | 9/1984 | Sugimoto |
| 4,568,344 A | | 2/1986 | Suzuki |
| 4,634,485 A | | 1/1987 | Welygan |
| 4,636,419 A | | 1/1987 | Madsen |
| 4,661,389 A | | 4/1987 | Mudge |
| 4,775,310 A | | 10/1988 | Fischer |
| 4,839,131 A | | 6/1989 | Cloeren |
| 4,842,794 A | | 6/1989 | Hovis |
| 4,894,060 A | | 1/1990 | Nestegard |
| 5,077,870 A | | 1/1992 | Melbye |
| 5,207,962 A | | 5/1993 | Hovis |
| 5,260,015 A | | 11/1993 | Kennedy |
| 5,290,377 A | | 3/1994 | Aihara |
| 5,366,782 A | | 11/1994 | Curro |
| 5,376,430 A | | 12/1994 | Swenson |
| 5,419,695 A | | 5/1995 | Clegg |
| 5,429,856 A | | 7/1995 | Krueger |
| D376,533 S | | 12/1996 | Akeno |
| 5,660,778 A | | 8/1997 | Ketcham |
| 5,679,302 A | | 10/1997 | Miller |
| 5,691,034 A | | 11/1997 | Krueger |
| 5,692,271 A | | 12/1997 | Provost |
| 5,776,343 A | | 7/1998 | Cullen |
| 5,845,375 A | | 12/1998 | Miller |
| 5,891,549 A | | 4/1999 | Beretta |
| 5,930,875 A | | 8/1999 | Schreiner |
| 6,039,911 A | | 3/2000 | Miller |
| 6,054,091 A | | 4/2000 | Miller |
| 6,106,922 A | | 8/2000 | Cejka |
| 6,132,660 A | | 10/2000 | Kampfer |
| 6,146,369 A | | 11/2000 | Hartman |
| 6,159,544 A | | 12/2000 | Liu |
| 6,190,594 B1 | | 2/2001 | Gorman |
| 6,240,817 B1 | | 6/2001 | James |
| 6,262,331 B1 | | 7/2001 | Nakahata |
| 6,287,665 B1 | | 9/2001 | Hammer |
| 6,391,420 B1 | | 5/2002 | Cederblad |
| 6,489,003 B1 | | 12/2002 | Levitt |
| 6,582,642 B1 | | 6/2003 | Buzzell |
| 6,627,133 B1 | | 9/2003 | Tuma |
| 6,669,887 B2 | | 12/2003 | Hilston |
| 6,767,492 B2 | | 7/2004 | Norquist |
| 7,001,475 B2 | | 2/2006 | Ausen |
| 7,014,906 B2 | | 3/2006 | Tuman |
| 7,048,818 B2 | | 5/2006 | Krantz |
| 7,048,984 B2 | | 5/2006 | Seth |
| 7,052,636 B2 | | 5/2006 | Ausen |
| 7,125,400 B2 | | 10/2006 | Igaue |
| 7,168,139 B2 | | 1/2007 | Seth |
| 7,182,992 B2 | | 2/2007 | Ausen |
| 7,185,401 B2 | | 3/2007 | Ausen |
| 7,198,743 B2 | | 4/2007 | Tuma |
| 7,214,334 B2 | | 5/2007 | Jens |
| 7,241,483 B2 | | 7/2007 | Ausen |
| 7,407,496 B2 | | 8/2008 | Petersen |
| 7,670,522 B2 | | 3/2010 | Ausen |
| 7,678,316 B2 | | 3/2010 | Ausen |
| 7,695,799 B2 | | 4/2010 | Cree |
| 7,748,090 B2 | | 7/2010 | Seth |
| 7,855,316 B2 | * | 12/2010 | Meyer et al. .................. 604/383 |
| 7,897,078 B2 | | 3/2011 | Petersen |
| 8,020,262 B2 | | 9/2011 | Oertel |
| 8,758,882 B2 | | 6/2014 | Ausen |
| 2002/0112325 A1 | | 8/2002 | Keohan |
| 2003/0008106 A1 | | 1/2003 | Guenther |
| 2003/0229326 A1 | | 12/2003 | Hovis |
| 2004/0147890 A1 | | 7/2004 | Nakahata |
| 2005/0271858 A1 | | 12/2005 | Ausen |
| 2007/0039142 A1 | | 2/2007 | Petersen |
| 2007/0134489 A1 | | 6/2007 | Neugebauer |
| 2007/0143972 A1 | * | 6/2007 | Kline .................... A44B 18/00 24/442 |
| 2007/0210477 A1 | | 9/2007 | Seth |
| 2007/0228605 A1 | | 10/2007 | Ausen |
| 2008/0009821 A1 | * | 1/2008 | Seth .................... A44B 18/0046 604/391 |
| 2009/0217492 A1 | | 9/2009 | Gallant |
| 2011/0084017 A1 | | 4/2011 | Pocher |
| 2011/0147475 A1 | | 6/2011 | Biegler |
| 2011/0151171 A1 | | 6/2011 | Biegler |
| 2011/0313389 A1 | | 12/2011 | Wood |
| 2012/0011685 A1 | | 1/2012 | Rocha |
| 2012/0204383 A1 | | 8/2012 | Wood |
| 2012/0330266 A1 | | 12/2012 | Zonneveld |
| 2013/0004723 A1 | | 1/2013 | Ausen |
| 2013/0004729 A1 | | 1/2013 | Ausen |
| 2013/0011600 A1 | | 1/2013 | Ausen |
| 2014/0050883 A1 | | 2/2014 | Hanschen |

(56) References Cited

U.S. PATENT DOCUMENTS

2014/0142533 A1    5/2014  Peltier
2014/0349062 A1   11/2014  Chandrasekaran

FOREIGN PATENT DOCUMENTS

| GB | 914489 | 1/1960 |
|----|--------|--------|
| GB | 1055963 | 1/1967 |
| GB | 1075487 | 7/1967 |
| GB | 2017485 | 10/1979 |
| WO | WO 94/02091 | 2/1994 |
| WO | WO 00/50229 | 8/2000 |
| WO | WO 2005/122818 | 12/2005 |
| WO | WO 2011/097436 | 8/2011 |
| WO | WO 2011/119323 | 9/2011 |
| WO | WO 2012/112768 | 8/2012 |
| WO | WO 2013/028654 | 2/2013 |
| WO | WO 2013/032683 | 3/2013 |
| WO | WO 2013/052371 | 4/2013 |
| WO | WO 2013/148128 | 10/2013 |
| WO | WO 2013/172957 | 11/2013 |
| WO | WO 2013/172960 | 11/2013 |
| WO | WO 2014/164242 | 10/2014 |

OTHER PUBLICATIONS

U.S. Application entitled, "Mechanical Fastener", filed Aug. 16, 2012, having U.S. Appl. No. 29/429,799.
International Search Report for PCT/US2014/038947, dated Sep. 16, 2014, 3 pages.

* cited by examiner

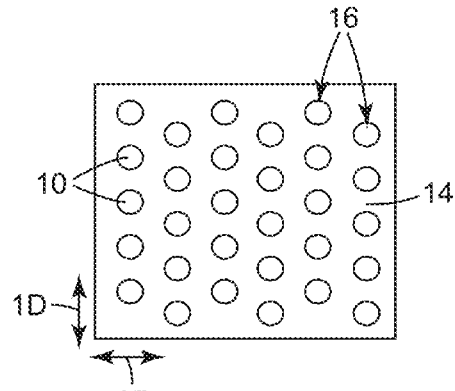
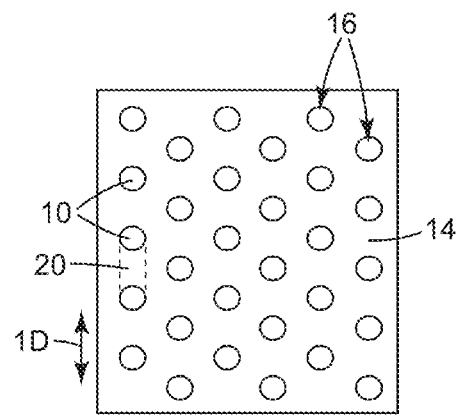
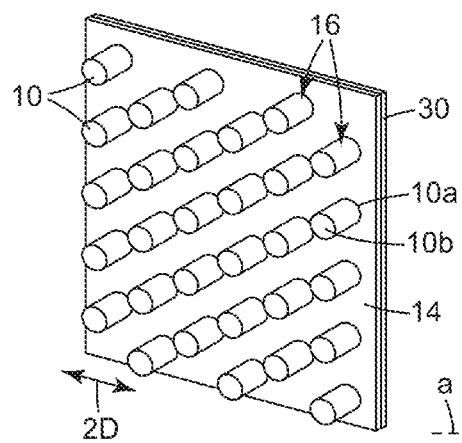
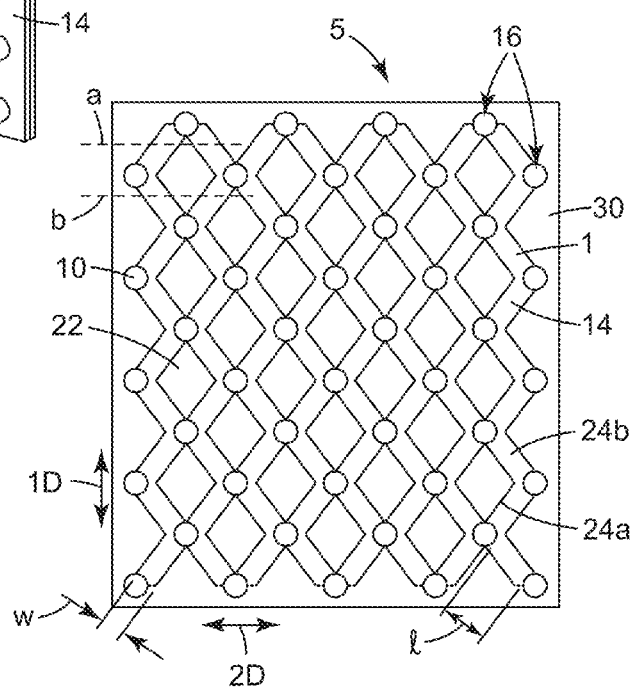
Fig. 1A
Fig. 1B
Fig. 1C
Fig. 1D

LAMINATES INCLUDING A RETICULATED THERMOPLASTIC FILM AND METHOD OF MAKING THE SAME

BACKGROUND

Articles with one or more structured surfaces are useful in a variety of applications (e.g., abrasive discs, assembly of automobile parts, and disposable absorbent articles). The articles may be provided as films that exhibit, for example, increased surface area, mechanical fastening structures, or optical properties.

Mechanical fasteners, which are also called hook and loop fasteners, typically include a plurality of closely spaced upstanding projections with loop-engaging heads useful as hook members, and loop members typically include a plurality of woven, nonwoven, or knitted loops. Mechanical fasteners are useful for providing releasable attachment in numerous applications. For example, mechanical fasteners are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Mechanical fasteners are also useful for disposable articles such as sanitary napkins. A sanitary napkin typically includes a back sheet that is intended to be placed adjacent to the wearer's undergarment. The back sheet may comprise hook fastener elements to securely attach the sanitary napkin to the undergarment, which mechanically engages with the hook fastener elements.

Some mechanical fasteners have been made with openings in the backing from which male fastening elements project. See, e.g., U.S. Pat. No. 4,001,366 (Brumlik) and U.S. Pat. No. 7,407,496 (Peterson), U.S. Pat. Appl. Pub. No. 2012/0204383 (Wood et al.), and Int. Pat. Appl. Pub. Nos. WO 2005/122818 (Ausen et al.) and WO 1994/02091 (Hamilton).

SUMMARY

The present disclosure provides a laminate of a reticulated film and a method of making a laminate. A reticulated film can be made on an extensible laminate simply by stretching a thermoplastic backing in a first direction, laminating the thermoplastic backing to an extensible carrier, and then stretching the laminate in a second direction perpendicular to the first direction. No slitting or aperturing of the film is needed before stretching. The method of making the laminate of the reticulated film takes advantage of the lower tear strength associated with stretch-induced molecular orientation of a film.

In one aspect, the present disclosure provides a laminate of an at least partially reticulated thermoplastic film joined to an extensible carrier. The reticulated thermoplastic film has a thermoplastic backing with first and second major surfaces, a plurality of openings in the thermoplastic backing, and a plurality of discrete elements protruding from the first major surface of the thermoplastic backing. There are two discrete elements, aligned in a first direction, abutting opposite ends of any given opening. In a second direction perpendicular to the first direction, there is one discrete element between the given opening and an adjacent opening aligned in the second direction. Each portion of the thermoplastic backing around the given opening is plastically deformed in its lengthwise direction.

In another aspect, the present disclosure provides a method of making a laminate. The method includes providing a thermoplastic backing having first and second major surfaces and a plurality of discrete elements protruding from the first major surface of the thermoplastic backing. At least some of the discrete elements are aligned in a row in a first direction. The method further includes stretching the thermoplastic backing in the first direction to plastically deform the thermoplastic backing and separate the at least some of the discrete elements aligned in the row in the first direction. The thermoplastic backing remains intact between the plurality of discrete elements after stretching it in the first direction. The method further includes laminating the thermoplastic backing to an extensible carrier to provide a laminate. The extensible carrier is extensible in at least a second direction perpendicular to the first direction. The method further includes stretching the laminate in a second direction perpendicular to the first direction. Stretching the laminate in the second direction forms a tear in the thermoplastic backing between two adjacent of the discrete elements aligned in the row in the first direction, and the tear is interrupted by the two adjacent of the discrete elements.

The method disclosed herein may be useful, in some embodiments, for making a reticulated mechanical fastening laminate web, strip, or patch that has a unique and attractive appearance. The method according to the present disclosure allows openings to be provided in the mechanical fastener without wasteful material loss. The openings can provide breathability and flexibility to the mechanical fastener, which may enhance the comfort of the wearer, for example, of an absorbent article comprising the mechanical fastener made by the method disclosed herein. The mechanical fastener also is typically able to cover a relatively large area with a relatively small amount of material, which may lower its cost. Also, because of the large area that may be covered by the mechanical fastener in an absorbent article, the mechanical fastener may provide performance enhancement, for example, by resisting shifting forces such as torsional or rotational forces caused by movement of the wearer of the absorbent article. For example, in use, fitting an absorbent article such as a diaper about the wearer usually requires the front and back waist portions of the diaper to overlap each other. As the diaper is worn the movements of the wearer tend to cause the overlapping front and back waist portions to shift position relative to each other. Unless such shifting is limited, the fit and containment characteristics of the diaper may be degraded as the diaper is worn. The mechanical fastener made according to the present disclosure may provide improved fit and closure stability by resisting such shifting because of its relatively larger area and flexibility.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure. It will be understood that, unless otherwise noted, those terms are used in their relative sense only. The designation of "first" and "second" may be applied to the major surfaces of the thermoplastic backing merely as a matter of convenience in the description of one or more of the embodiments.

By using words of orientation such as "overlying" and "underlying" and versions thereof for the location of various elements in the disclosed laminates, we refer to the relative position of an element with respect to a horizontally-disposed laminate with an upwardly-facing reticulated film. It is not intended that the laminates should have any particular orientation in space during or after manufacture.

The terms "multiple" and "a plurality" refer to more than one.

The term "opening" should be understood to be a void space that is surrounded by the thermoplastic backing. The opening may or may not enclose fibrils of the thermoplastic backing, which typically have a width that is less than 10 percent or less than 5 percent of the width of each portion of the thermoplastic backing around the opening.

In some embodiments, the reticulated film according to the present disclosure is a continuous or running web, sometimes having an indefinite length. A web can typically be handled in a roll-to-roll process. In some embodiments, the method according to the present disclosure is carried out on a continuous web. The term "machine direction" (MD) as used herein denotes the direction of a running web of material during a manufacturing process. When a strip is cut from a continuous web, the machine direction corresponds to the length "L" of the strip. The terms "machine direction" and "longitudinal direction" may be used interchangeably. The term "cross-machine direction" (CD) as used herein denotes the direction which is essentially perpendicular to the machine direction. When a strip is cut from a continuous web, the cross-machine direction corresponds to the width "W" of the strip. In some embodiments of the method disclosed herein, the first direction is the machine direction, and the second direction is the cross-machine direction, but this is not a requirement.

The term "extensible" refers to a material that can be extended or elongated in the direction of an applied stretching force without destroying the structure of the material or material fibers. An elastic material is an extensible material that has recovery properties. In some embodiments, an extensible material may be stretched to a length that is at least about 5, 10, 15, 20, 25, or 50 percent greater than its relaxed length without destroying the structure of the material or material fibers.

The term "elastic" refers to any material (such as a film that is 0.002 mm to 0.5 mm thick) that exhibits recovery from stretching or deformation. In some embodiments, a material may be considered to be elastic if, upon application of a stretching force, it can be stretched to a length that is at least about 25 (in some embodiments, 50) percent larger than its initial length and can recover at least 40, 50, 60, 70, 80, or 90 percent of its elongation upon release of the stretching force.

The term "non-elastic" refers to any material (such as a film that is 0.002 mm to 0.5 mm thick) that does not exhibit recovery from stretching or deformation to a large extent. For example, a non-elastic material that is stretched to a length that is at least about 50 percent greater than its initial length will recover less than about 40, 25, 20, or 10 percent of its elongation upon release of its stretching force. In some embodiments, a non-elastic material may be considered to be a flexible plastic that is capable of undergoing permanent plastic deformation if it is stretched past its reversible stretching region.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which:

FIG. 1A is a top view of one embodiment of a film useful for the method of making a laminate according to the present disclosure;

FIG. 1B is a top view of the film shown in FIG. 1A after it has been stretched in a first direction;

FIG. 1C is a perspective view of a film shown in FIG. 1B laminated to an extensible carrier;

FIG. 1D is a top view of an embodiment of a laminate according to the present disclosure, which, according to some embodiments of the method according to the present disclosure, is prepared by stretching the film shown in FIG. 1B in a second direction perpendicular to the first direction;

DETAILED DESCRIPTION

Figure 2:
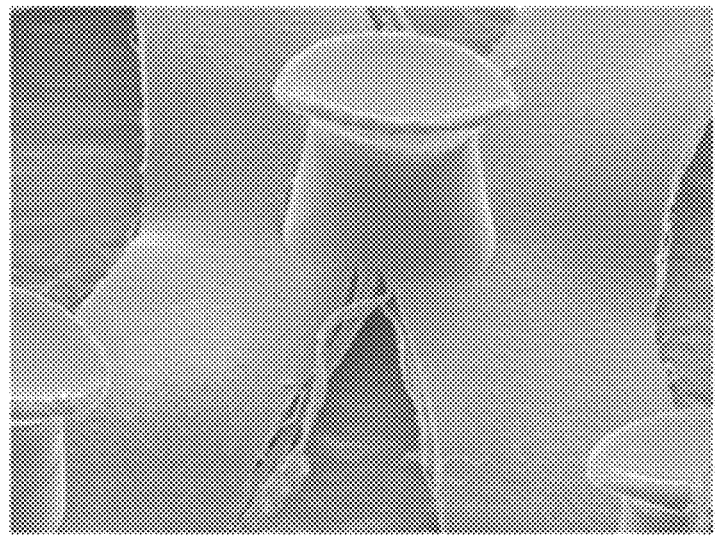
FIG. 2 is a scanning electron micrograph showing a perspective view of a portion of a reticulated film similar to that shown in FIG. 1D.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

FIG. 1A shows a top view of an embodiment of a thermoplastic backing 14 with discrete elements 10 protruding from the first major surface of the backing, which is the major surface visible in the drawing.

FIG. 1B illustrates the result of stretching the thermoplastic backing 14 in the first direction 1D, which is a feature of the method according to the present disclosure. FIG. 1B illustrates that the discrete elements 10 are spaced further apart in first direction 1D after stretching. Although not shown in the drawing, the thermoplastic backing 14 becomes thinner, is plastically deformed, and has stretch-induced molecular orientation in the first direction 1D. However, the thermoplastic backing 14 remains intact between the discrete elements 10 after stretching. In other words, the thermoplastic backing 14 does not have a plurality of any of cuts, slits, tears, or apertures after stretching in the first direction; instead the backing remains a continuous film. During the stretching in the first direction, the discrete elements 10 formed in the thermoplastic backing 14 resist stretching. At their bases, the areas of the discrete elements 10 behave as thicker portions of film and do not stretch to the same extent as the thermoplastic backing 14 on either side. To compensate for this resistance to stretching of the bases, at least a portion of the area 20 of the thermoplastic backing between the discrete elements 10 is believed to stretch to a greater extent than the thermoplastic backing 14 on either side. The regions of the thermoplastic backing 14 with the highest stretch-induced molecular orientation in the first direction 1D are therefore found within areas 20 between the discrete elements 10.

FIG. 1C is a perspective view of a laminate of the thermoplastic backing 14 with discrete elements 10 shown in FIG. 1B laminated to an extensible carrier 30. In some embodiments, at least some of the discrete elements comprise one upstanding post. In some embodiments, at least some of the discrete elements 10 are upstanding posts on the thermoplastic backing 14, which typically have proximal ends 10a and distal ends 10b, with the proximal end including the base that is attached to the thermoplastic backing 14, and the distal end extending away from the thermoplastic backing. The extensible carrier 30 is extensible at least in the second direction 2D and is generally selected such that it has a lower yield point than that of the thermoplastic backing 14 with discrete elements 10.

FIG. 1D illustrates the result of stretching the laminate 5 in the second direction 2D, which is a feature of the method according to the present disclosure. Second direction 2D is perpendicular to first direction 1D. Since the areas 20 shown in FIG. 1B have the highest stretch-induced molecular orientation in the thermoplastic backing 14 in the first direction, they have the lowest tear resistance. Stretching the laminate 5 in the second direction 2D causes the thermoplastic backing 14 to tear in areas 20 to provide the openings 22 in the thermoplastic backing 14 as shown in FIG. 1D. The tears in areas 20 are interrupted by the discrete elements 10 on either end of areas 20. A discrete element according to some embodiments of the method according to the present disclosure that interrupts tear propagation is shown in the scanning electron micrograph of FIG. 2 although this micrograph is of a backing that was not stretched while laminated to an extensible carrier. In some embodiments, including the embodiment shown in FIG. 2, the discrete elements protrude only from the first major surface of the thermoplastic backing. It should be understood that the thermoplastic backing 14 shown in FIG. 1C is not slit or apertured. Instead, openings 22 are formed in the thermoplastic backing 14 simply by stretching the thermoplastic backing 14 in the first direction 1D and then stretching the laminate shown in FIG. 1C in the second direction 2D.

Although stretching the film shown in FIG. 1B in the second direction 2D can be carried out without laminating it to an extensible carrier, stretching the laminate shown in FIG. 1C in the second direction 2D can be carried out more quickly. When stretching the film shown in FIG. 1B in the second direction, each tear induces a weak point in the thermoplastic backing, and the stretching forces become exerted only on the portions of the thermoplastic backing between the openings, with high stress exerted on the thermoplastic backing at the positions of the discrete elements. In the laminate 5 shown in FIG. 1D, the stretching forces are exerted mainly on the extensible carrier 30. As a result, stretching a laminate in the second direction 2D can be carried out at least ten times faster than stretching the thermoplastic film itself.

FIG. 1D also illustrates an embodiment of a laminate 5 according to the present disclosure. In the embodiment illustrated in FIG. 1D, the thermoplastic backing 14 has a staggered array of discrete elements 10 protruding from its first major surface when viewed in either the first direction 1D or the second direction 2D. A staggered array may appear to be a square array depending on the angle of viewing; therefore, the angle of viewing is specified. In some embodiments, a staggered array is an array that appears staggered when viewed from the first direction. Referring again to the embodiment of the method illustrated in FIGS. 1A-1D, discrete elements 10 are aligned in rows 16 in the first direction 1D but are staggered in the second direction 2D.

In the reticulated film 1 shown in FIG. 1D, for any given single opening 22 in the reticulated film, there are four discrete elements 10 around the single opening 22. Two discrete elements 10 abut the opening on opposite ends, which are the discrete elements that serve to interrupt the tears formed in the thermoplastic backing upon stretching in the second direction 2D in the method disclosed herein. The remaining two discrete elements of the four discrete elements around the opening have a portion of thermoplastic backing 14 between them and the opening 22. There is one discrete element between the given opening and an adjacent opening aligned in the second direction. In some embodiments, when two openings are said to be aligned, they are aligned along an axis of symmetry. No portion of the thermoplastic backing 14 connects either of the two pairs of opposing discrete elements 10 in the group of four discrete elements.

Furthermore, between any two adjacent openings, there is generally up to one discrete element protruding from the thermoplastic backing. That is, there may be zero or one discrete element between any two adjacent openings. For the purposes of the present disclosure, to determine whether a discrete element is between two adjacent openings, the discrete element must be located somewhere on the portion of the thermoplastic backing that separates the two adjacent openings. When viewed down rows 16, the reticulated film 1 clearly has one discrete element 10 between any two adjacent openings 22. Also, when viewed in direction 2D, which is perpendicular to rows 16, the reticulated film 1 clearly has one discrete element 10 between any two adjacent openings 22. Thus, when viewed along an axis of symmetry along which a plurality of openings is aligned, there is one discrete element 10 between any two adjacent openings. However, when viewed at a 45 degree angle to rows 16, the reticulated film 1 may be considered to have no discrete element 10 between any two adjacent openings 22 since the discrete elements 10 are not located in the portion of the thermoplastic backing 14 that separates the two openings 22. In some embodiments, including the embodiment shown in FIG. 1C, there appears to be exactly one discrete element 10 at every intersection in the reticulated film 1. An opening and the associated portions of thermoplastic backing that surround it can be referred to as the unit cell of the reticulated film. In some embodiments, including the embodiment shown in FIG. 1D, the unit cell has four sides and four angles, and there appears to be exactly one discrete element 10 associated with each angle in the unit cell.

In laminates made according to the method disclosed herein, the reticulated film typically has other unique features. Because the thermoplastic backing is first stretched in the first direction 1D, each portion of the thermoplastic backing 14 defined by a width dimension "w" and a length dimension "l" is plastically deformed in its lengthwise direction. As used herein the terms "length" or "lengthwise" typically refer to the longest dimension of the portion of the thermoplastic backing between openings although the original density and dimensions of the discrete elements and the degree of stretching in the first direction can alter the dimensions of the thermoplastic backing portions. The lengthwise direction may also be considered the first direction when the openings are retracted or closed such as when the extensible carrier is elastic and in its retracted state or when the reticulated film is removed from the non-elastic extensible carrier and tension is applied in the first direction to at least partially close the openings. As used herein the term "width" typically refers to the shortest dimension in the plane of the thermoplastic backing of the portion of the backing between openings. The width dimension may also be considered parallel to the second direction when the openings are retracted or closed. Each portion of the thermoplastic backing typically has a greater stretch-induced molecular orientation in the length dimension than in the width dimension. There may be no stretch-induced molecular orientation in the width dimension "w" because the thermoplastic backing tears instead of stretching when extended in the second direction, or there may be some localized stretch-induced molecular orientation in the width dimension at connection points. Also, the thickness of the thermoplastic backing 14 can be substantially uniform in the reticulated film 1. The thickness of the thermoplastic backing 14 after stretching in the first direction 1D as shown in FIG. 1B is the same as the thickness of the thermoplastic backing 14 after stretching in the second direction 2D as shown in FIG. 1D again because the thermoplastic backing tears instead of stretching when extended in the second direction.

Figure 3A:
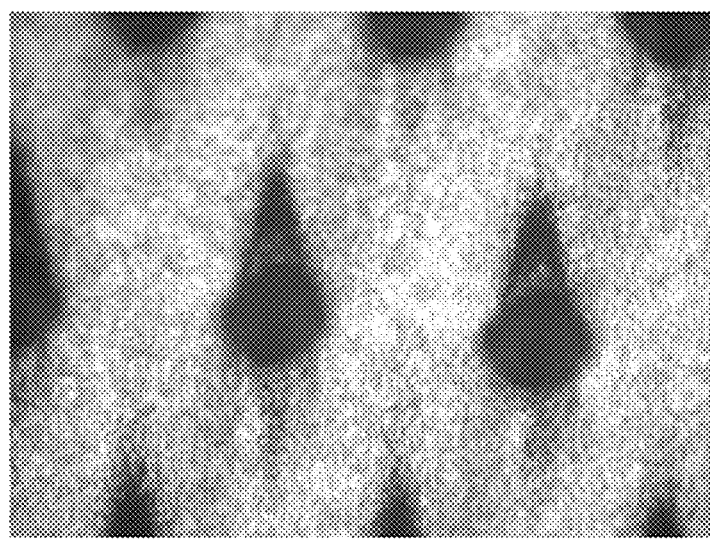
FIG. 3A is a photograph taken with a polarization microscope equipped with cross polars of a film such as that shown in FIG. 1B after it has been stretched in a first direction.
Figure 3B:
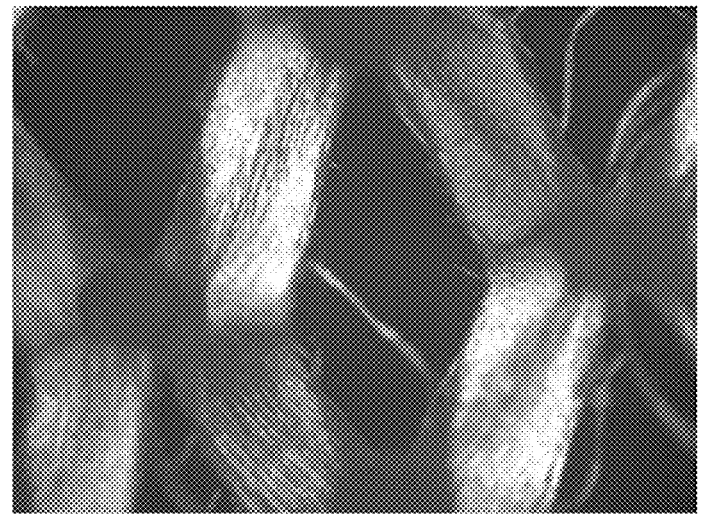
FIG. 3B is a photograph taken with a polarization microscope equipped with cross polars of the film shown in FIG. 3A after it has been stretched in a second direction perpendicular to the first direction.

Stretch-induced molecular orientation in the reticulated film according to the present disclosure can be determined by standard spectrographic analysis of the birefringent properties of the thermoplastic backing in the reticulated film. Each portion of the thermoplastic backing between the openings in the reticulated film may also be understood to be birefringent, which means that the polymer in the thermoplastic backing has different effective indexes of refraction in different directions. As described above in connection with FIG. 1B, stretch-induced molecular orientation in the thermoplastic backing 14 is believed to be highest within areas 20. A photograph taken with a polarization microscope equipped with cross polars, shown in FIG. 3A, illustrates this point. In the gray scale image shown in FIG. 3A, the darker, triangular area above and below the round upstanding elements reveals that the highest birefringence in the film is between the discrete elements. FIG. 3B is a photograph taken of the film shown in FIG. 3A after is has been stretched in the second direction. FIG. 3B illustrates that the birefringence that results from the stretch-induced molecular orientation in the thermoplastic backing of the reticulated film is highest where it abuts an opening. The lighter color on the edges of each portion of the thermoplastic backing shown in FIG. 3B reveals higher birefringence at or near the edges than in the center portion of the thermoplastic backing. Referring again to FIG. 1D, birefringence from stretch-induced molecular orientation is typically higher at the position 24a at the edge of an opening than in a portion of the thermoplastic backing that does not abut an opening, for example, at 24b or at a mid-point of the portion of the thermoplastic backing. Although not visible in the gray scale image of FIG. 3B, the highest birefringence is located in the thermoplastic backing on the edge of the opening near the location of the discrete element.

The higher stretch-induced molecular orientation at a location at the edge of a given opening would not be observed in a backing that is slit, apertured, or molded to have openings. In cases where stretching follows slitting, aperturing, or molding an opening, for example, stretching would not preferentially occur at the slit, aperture, or opening to provide increased birefringence at that location. At a slit, aperture, or molded opening, there is an interruption in material and therefore no material to transmit the stretching force. Therefore, there is no reason to believe that a higher level of stretch-induced molecular orientation would be observed at the edge of an opening than toward the center of a portion of a thermoplastic backing between openings.

In many embodiments, including the embodiment that is shown in FIG. 3B, at least one (in some embodiments, each) portion of the thermoplastic backing that surrounds a given opening has a similar profile across its width of higher birefringence toward the opening and lower birefringence toward the center of each portion of the thermoplastic backing.

To determine whether a reticulated film has generally higher stretch-induced molecular orientation in a portion of the thermoplastic backing near the edge of a given opening than in the center of the portion and/or to determine whether each portion of the thermoplastic backing that surrounds a given opening has a similar profile across its width of higher birefringence toward the opening, a polarization microscope such as a "LEICA DM2700P", obtained from Microsystems GmbH, Wetzlar, Germany, equipped with cross polars is used in transmission mode. The polarizer and analyzer are placed at 90 degrees to each other such that the field of view is dark. The sample is placed between the polarizer and analyzer, and the image is recorded using an image capturing device.

Figure 3C:
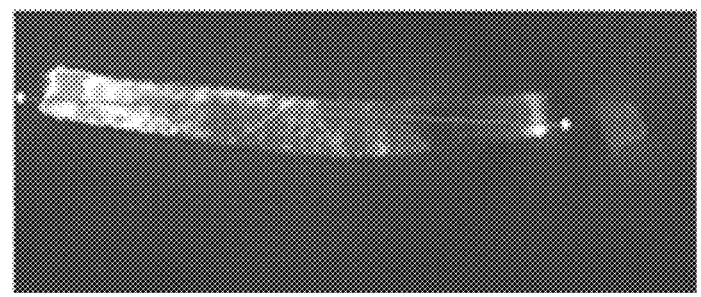
FIGS. 3C and 3D are micrographs showing optical retardance maps of two portions of the thermoplastic backing between openings in a reticulated film according to the present disclosure.
Figure 3D:
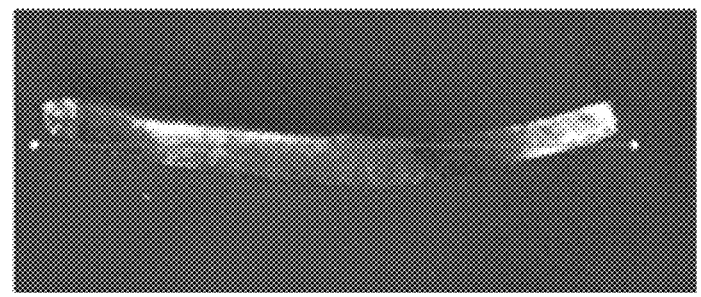

Also, higher birefringence at the edges of each portion of the thermoplastic backing in reticulated films disclosed herein is shown by cross sectioning the portions of the thermoplastic backing and measuring birefringence. Referring again to FIG. 1D, a unit cell in reticulated film 1 was cut in 2D in two places "a" and "b" to cut through each portion of the thermoplastic backing in the cell. A cross-section of each cut portion was photographed to show the optical retardance map of each sample. Two of the photographs are shown in FIGS. 3C and 3D. Areas of lighter color indicate areas of higher birefringence. In the photographs shown in FIGS. 3C and 3D, the highest birefringence is observed at one edge of each cross-section. The birefringence in these samples was measured with a retardance imaging system available from Lot-Oriel GmbH & Co., Darmstadt, Germany, under the trade designation "LC-PolScope" on a microscope available from Leica Microsystems GmbH, under the trade designation "DMRXE" and a digital CCD color camera available from QImaging, Surrey, BC, Canada, under the trade designation "RETIGA EXi FAST 1394". The microscope was equipped with a 546.5 nm interference filter obtained from Cambridge Research & Instrumentation, Inc., Hopkinton, Mass., and a 10×/0.25 objective.

In some embodiments of the laminate according to the present disclosure, the carrier also has stretch induced molecular orientation if it is plastically deformed upon stretching in the second direction 2D. The carrier may have higher stretch-induced molecular orientation in the second direction 2D than in the first direction 1D. Stretch-induced molecular orientation in the carrier can also be determined by standard spectrographic analysis of its birefringent properties using either of the techniques described above.

For some embodiments of the reticulated film disclosed herein, particularly embodiments in which the extensible carrier is non-elastic or when the extensible carrier is elastic and stretched, the openings formed in the thermoplastic backing are in the form of a repeating pattern of quadrilaterals. The quadrilaterals generally have two axes of symmetry, one in 1D and one in 2D. In some embodiments, the openings are in the shape of rhombuses. Again, no portion of the thermoplastic backing bridges between opposing angles of the quadrilaterals. Extensible carriers that are elastic may have retraction force that closes the openings once they are made. In these embodiments, when the stretching force is released, and the elastic is in its relaxed state, the openings may be very narrow and appear as slits. There may be more than one repeating pattern of quadrilateral-shaped openings or slits, for example, if the discrete elements are not evenly spaced on the thermoplastic backing. There may be zones in the thermoplastic backing having different spacings of the discrete elements, giving rise to different sizes of the discrete openings. For discrete elements that are evenly spaced, the spacing (e.g., distance in the CD) between the discrete openings may differ by up to 10, 5, 2.5, or 1 percent.

In the laminate according to the present disclosure, the reticulated film may be partially reticulated, for example, in embodiments in which only a portion of the extensible carrier is stretched.

The thermoplastic backing in the reticulated film 1 in the laminate according to the present disclosure and in its precursors in the method according to the present disclosure is substantially planar. A substantially "planar" reticulated film refers to the portions of thermoplastic backing or strands occupying substantially the same plane when placed on a flat surface. The term "substantially" in this regard can mean that a portion of the thermoplastic backing may be out of plane by up to 15, 10, or 5 degrees. A thermoplastic backing that is substantially planar is not corrugated and not profile-extruded to have multiple peaks and valleys. The various portions of the thermoplastic backing also do not cross over each other, for example, at intersections of the reticulated film in a "substantially planar" film.

Although FIGS. 1A through 1D illustrate an embodiment of the method according to the present disclosure in which the discrete elements 10 are aligned in rows 16 in the first direction 1D, which is the direction of the first stretch, other relationships between the discrete elements and the first direction may be useful. For example, for a thermoplastic backing having a square array of discrete elements, the first direction may be at a 45 degree angle to a given row of discrete elements. A second stretch in a second direction perpendicular to the first direction after joining the thermoplastic backing to a carrier will provide openings in the thermoplastic backing.

Figure 4:
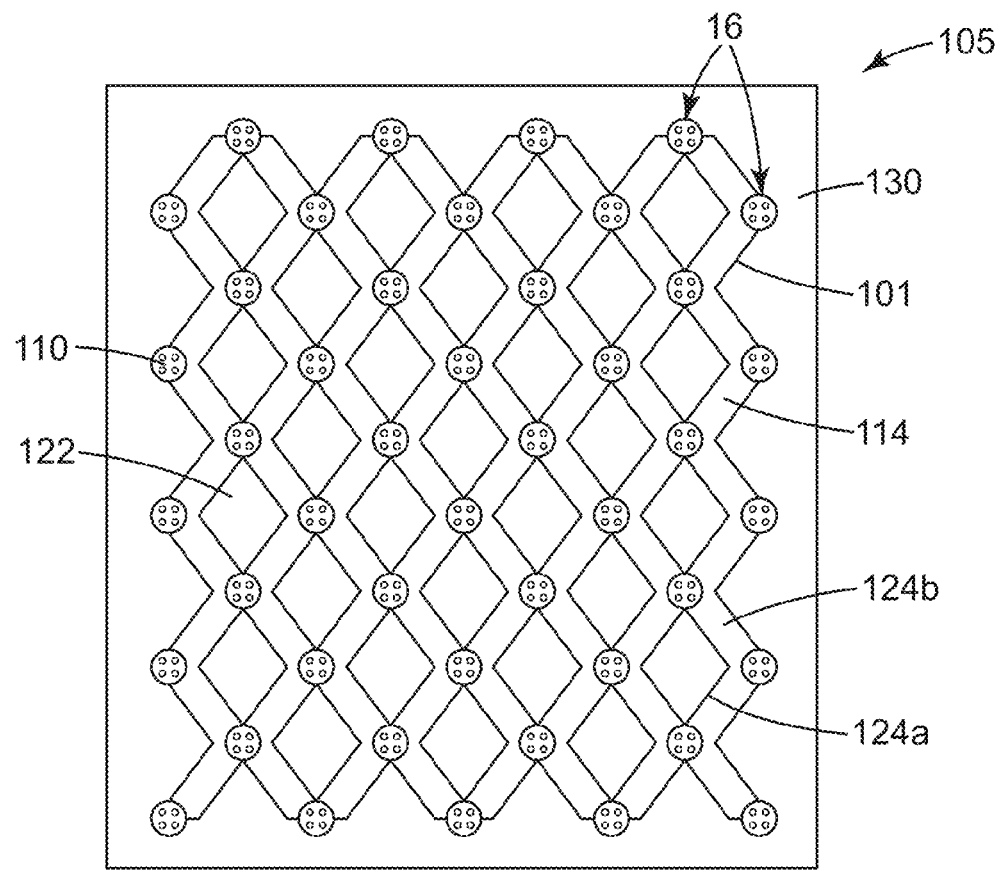
FIG. 4 is a top view of another embodiment of a laminate according to the present disclosure.

FIG. 4 illustrates another embodiment of the laminate according to the present disclosure. The reticulated film 101 laminated to carrier 130 in laminate 105 has a staggered array of discrete elements 110 protruding from the first major surface of the thermoplastic backing. In the illustrated embodiment, the discrete elements 110 comprise multiple upstanding posts on a surface protrusion. The upstanding posts each have proximal ends and distal ends, with the proximal end including the base that is attached to the surface protrusion, and the distal end extending away from the thermoplastic backing. As in the reticulated film shown in the embodiment of FIG. 1D, between any two adjacent openings 122, there is up to one discrete element 110 protruding from the thermoplastic backing; there is exactly one discrete element 110 at every intersection in the reticulated film 101. Also, in the illustrated embodiment, for any given single opening 122 in the reticulated film 101, there are four discrete elements 110 around the single opening 122, with two discrete elements 110 abutting the opening 122 on opposite ends and the remaining two discrete elements of the four discrete elements around the opening having a portion of thermoplastic backing 114 between them and the opening 122. There is one discrete element between the given opening 122 and an adjacent opening aligned in the second direction. The stretch-induced molecular orientation in the thermoplastic backing 114 of reticulated film 101 is typically highest where it abuts an opening, for example, at 124*a*. In other words, the stretch-induced molecular orientation is typically higher at the position 124*a* than in a portion of the thermoplastic backing that does not abut an opening, for example, at 124*b*. Moreover, each portion of the thermoplastic backing that surrounds a given opening has a similar profile across its width of higher birefringence toward the opening and lower birefringence toward the center.

Various features of thermoplastic backing having discrete elements protruding therefrom (such as that shown in FIG. 1A) can influence the method according to the present disclosure and also can affect the appearance and properties of the resultant laminate. For example, the thickness of the thermoplastic backing is related to the degree of stretching (that is, draw ratio) in the first direction that is required to cause area 20 (shown in FIG. 1B) to tear upon stretching in the second direction. The term "draw ratio" refers to ratio of a linear dimension of a given portion of the thermoplastic backing after stretching to the linear dimension of the same portion before stretching. The method according to the present disclosure can be useful with thermoplastic backings having a variety of thicknesses. In some embodiments, the thickness of the thermoplastic backing suitable for the method disclosed herein may be up to about 400 micrometers, 300 micrometers, or 250 micrometers and at least about 30 micrometers or 50 micrometers before stretching in the first direction, depending on the desired reticulated film in the laminate. This thickness does not include the height of the discrete elements protruding from the first major surface of the thermoplastic backing. In some embodiments, the thickness of the thermoplastic backing is in a range from 30 to about 225 micrometers, from about 50 to about 200 micrometers, or from about 50 to about 150 micrometers before stretching in the first direction. Thin films will require a lower draw ratio in the first direction than thicker films to provide the desired amount of stretch-induced molecular orientation in area 20. The selection of material for the thermoplastic backing also impacts the draw ratio. For a polypropylene or polyethylene backing, the draw ratio in the first direction sufficient to provide the desired amount of stretch-induced molecular orientation in area 20 can be 1.25, 1.5, 2.0, 2.25, 2.5, 2.75, or 3, depending on the thickness of the backing and the temperature of the backing when it is stretched. For example, the draw ratio in the first direction for a backing 70 micrometers thick may be about 2, the draw ratio in the first direction for a backing 100 micrometers thick may be in a range from about 2.2 to 2.5, and the draw ratio in the first direction for a backing 130 micrometers thick may be in a range from about 2.5 to 2.75 when stretching any of these backings is carried out at a temperature in a range from 85° C. to 130° C., for example. The maximum draw ratio is limited by the tensile strength of the selected material. Draw ratios of up to 5, 7.5, or 10 may be useful, depending on material selection and the temperature of the thermoplastic backing when it is stretched.

The width of the discrete element 10 or 110 at its base (that is, the point where it begins to protrude from the thermoplastic backing) also can influence the method according to the present disclosure. The term "width dimension" should be understood to include the diameter of a discrete element 10 with a circular cross-section. The discrete element 10 may have more than one width dimension (e.g., in a rectangular or elliptical cross-section shaped post). Furthermore, the discrete element 10 may taper, for example, from the proximal end at the base toward the distal end, as shown in FIG. 2. In these cases, the width of the discrete element is considered to be its greatest width at its base. The width of discrete elements affects their resistance to stretching in the first direction and therefore affects the amount of increased stretching in area 20 of the thermoplastic backing between the discrete elements 10 relative to the thermoplastic backing 14 on either side. In some embodiments, the discrete element has a width that is at least as big as the thickness of the film as described in any of the embodiments listed above. The discrete elements 10 may have a cross-section with a maximum width dimension "w" of at least 30 micrometers, 50 micrometers, 70 micrometers, 100 micrometers, or 125 micrometers. The width of the discrete element 10 may be up to 1 millimeter in some embodiments. In some embodiments, the discrete elements 10 have a cross-section with a width dimension "w" in a range from 70 micrometers to 500 micrometers or 100 micrometers to 400 micrometers.

The draw ratio and the width of the discrete elements 10 or 110 at the base also influence the appearance and/or properties of the resultant reticulated film in the laminate, for example, width of the portions (or strands) of the thermoplastic backing 14 or 114 and basis weight of the reticulated film. For a given film, a higher draw ratio provides lower strand widths and lower basis weight nets. Wider discrete elements also provide lower strand widths.

The density of the discrete elements 10 or 110 on the thermoplastic backing 14 or 114 also influences the appearance and/or properties of the reticulated film in the laminate according to the present disclosure. A variety of densities of the discrete elements may be useful, and for a given film, a higher density of discrete elements provides lower strand widths in the reticulated film. In some embodiments, the density of discrete elements on the thermoplastic backing is in a range from 20 per $cm^2$ to 1000 per $cm^2$ (in some embodiments, in a range from 20 per $cm^2$ to 500 per $cm^2$, 50 per $cm^2$ to 500 per $cm^2$, 60 per $cm^2$ to 400 per $cm^2$, 75 per $cm^2$ to 350 per $cm^2$, 100 per $cm^2$ to 300 per $cm^2$, or 200 per $cm^2$ to 1000 per $cm^2$).

The discrete element protruding from the thermoplastic backing in the method and laminate according to the present disclosure may have a variety of heights. The discrete element useful for providing resistance to stretching in the method according to the present disclosure may have a height above the thermoplastic backing of at least 30 micrometers. In some embodiments, the discrete elements have a maximum height (above the backing) of up to 3 mm, 1.5 mm, 1 mm, or 0.5 mm and, in some embodiments a minimum height of at least 50 micrometers, 100 micrometers, or 200 micrometers. In some embodiments, the discrete elements have an aspect ratio (that is, a ratio of height to width at the widest point) of at least about 0.25:1, 1:1, 2:1, 3:1, or 4:1.

It should be understood from the present disclosure that the discrete elements refer to elements that are separate and distinct from each other. They are not part of a continuous ridge or rib in thermoplastic backing, either before or after stretching. Furthermore, the discrete elements are separate and distinct from the thermoplastic backing. In some embodiments, the thermoplastic backing, excluding the discrete elements, is substantially uniform in thickness. For a thermoplastic backing that is substantially uniform in thickness, a difference in thickness between any two points in the thermoplastic backing may be up 5, 2.5, or 1 percent.

The thermoplastic backing useful for practicing the method disclosed herein and useful for the resulting reticulated film in the laminate may be made from a variety of suitable materials. Suitable thermoplastic materials include polyolefin homopolymers such as polyethylene and polypropylene, copolymers of ethylene, propylene and/or butylene; copolymers containing ethylene such as ethylene vinyl acetate and ethylene acrylic acid; polyesters such as poly (ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. In some embodiments, the thermoplastic is a polyolefin (e.g., polyethylene, polypropylene, polybutylene, ethylene copolymers, propylene copolymers, butylene copolymers, and copolymers and blends of these materials). For any of the embodiments in which the thermoplastic backing includes polypropylene, the polypropylene may include alpha and/or beta phase polypropylene. In some cases, a thermoplastic backing such as that shown in FIGS. 1A and 1B that includes beta-phase polypropylene before stretching in the first direction 1D may include alpha-phase polypropylene after stretching. Since the reticulated film in the laminate according to the present disclosure and/or made according to the present disclosure has a thermoplastic backing that is plastically deformed, it should be understood that the thermoplastic backing is generally non-elastic.

In some embodiments, the thermoplastic backing 14 or 114 with discrete elements 10 or 110 can be made from a multilayer or multi-component melt stream of thermoplastic materials. This can result in discrete elements formed at least partially from a different thermoplastic material than the one predominately forming the backing. Various configurations of upstanding posts made from a multilayer melt stream are shown in U.S. Pat. No. 6,106,922 (Cejka et al.), for example. A multilayer or multi-component melt stream can be formed by any conventional method. A multilayer melt stream can be formed by a multilayer feedblock, such as that shown in U.S. Pat. No. 4,839,131 (Cloeren). A multicomponent melt stream having domains or regions with different components could also be used. Useful multicomponent melt streams could be formed by use of inclusion co-extrusion die or other known methods (e.g., that shown in U.S. Pat. No. 6,767,492 (Norquist et al.).

For the method and laminate according to the present disclosure, the thermoplastic backing and the discrete elements are integral (that is, generally formed at the same time as a unit, unitary). Discrete elements such as upstanding posts on a backing can be made, for example, by feeding a thermoplastic material onto a continuously moving mold surface with cavities having the inverse shape of the discrete elements. The thermoplastic material can be passed between a nip formed by two rolls or a nip between a die face and roll surface, with at least one of the rolls having the cavities. Pressure provided by the nip forces the resin into the cavities. In some embodiments, a vacuum can be used to evacuate the cavities for easier filling of the cavities. The nip has a large enough gap such that a coherent thermoplastic backing is formed over the cavities. The mold surface and cavities can optionally be air or water cooled before stripping the integrally formed backing and upstanding posts from the mold surface such as by a stripper roll.

Suitable mold surfaces for forming discrete elements that include one upstanding post include tool rolls such as those formed from a series of plates defining a plurality of cavities about its periphery including those described, for example, in U.S. Pat. No. 4,775,310 (Fischer). Cavities may be formed in the plates by drilling or photoresist technology, for example. Other suitable tool rolls may include wire-wrapped rolls, which are disclosed along with their method of manufacturing, for example, in U.S. Pat. No. 6,190,594 (Gorman et al.). Another example of a method for forming a thermoplastic backing with upstanding posts includes using a flexible mold belt defining an array of upstanding post-shaped cavities as described in U.S. Pat. No. 7,214,334 (Jens et al.). Yet other useful methods for forming a thermoplastic backing with upstanding posts can be found in U.S. Pat. No. 6,287,665 (Hammer), U.S. Pat. No. 7,198,743 (Tuma), and U.S. Pat. No. 6,627,133 (Tuma).

While in some embodiments, at least some of the discrete elements on the thermoplastic backing comprise one upstanding post, in other embodiments, at least some of the discrete elements comprise multiple upstanding posts on a surface protrusion. In these embodiments, the discrete elements can be made by a modification of the mold surface described above, in which the cavity includes a main cavity with multiple smaller cavities within the main cavity.

In any of the mold surfaces mentioned above, the cavities and the resultant discrete elements may have a variety of cross-sectional shapes. For example, the cross-sectional shape of the cavity and discrete element may be a polygon (e.g., square, rectangle, rhombus, hexagon, pentagon, or dodecagon), which may be a regular polygon or not, or the cross-sectional shape of the post may be curved (e.g., round or elliptical). The discrete element may taper from its base to its distal tip, for example, for easier removal from the cavity, but this is not a requirement. The cavity may have the inverse shape of a post having a loop-engaging head (e.g., a male fastening element) or may have the inverse shape of an upstanding post without loop-engaging heads that can be formed into loop-engaging heads, if desired.

If upstanding posts formed upon exiting the cavities do not have loop-engaging heads, loop-engaging heads could be subsequently formed by a capping method as described in U.S. Pat. No. 5,077,870 (Melbye et al.). Typically, the capping method includes deforming the tip portions of the upstanding posts using heat and/or pressure. The heat and pressure, if both are used, could be applied sequentially or simultaneously. The formation of male fastening elements can also include a step in which the shape of the cap is changed, for example, as described in U.S. Pat. No. 6,132,660 (Kampfer). Such capping and cap modification steps can be carried out before or after stretching in the first direction or before or after stretching in the second direction in the method of making a laminate disclosed herein.

For any of the embodiments described above in which the discrete elements are upstanding posts with loop-engaging overhangs, the term "loop-engaging" relates to the ability of a male fastening element to be mechanically attached to a loop material. Generally, male fastening elements with loop-engaging heads have a head shape that is different from the shape of the post. For example, the male fastening element may be in the shape of a mushroom (e.g., with a circular or oval head enlarged with respect to the stem), a hook, a palm-tree, a nail, a T, or a J. In some embodiments, each discrete element includes an upstanding post and a cap with loop engaging overhangs extending in multiple (i.e., at least two) directions, in some embodiments, at least two orthogonal directions. For example, the upstanding post may be in the shape of a mushroom, a nail, a palm tree, or a T. In some embodiments, the upstanding posts are provided with a mushroom head (e.g., with an oval or round cap distal from the thermoplastic backing). The loop-engageability of male fastening elements may be determined and defined by using standard woven, nonwoven, or knit materials. A region of male fastening elements with loop-engaging heads generally will provide, in combination with a loop material, at least one of a higher peel strength, higher dynamic shear strength, or higher dynamic friction than a region of posts without loop-engaging heads. Male fastening elements that have "loop-engaging overhangs" or "loop-engaging heads" do not include ribs that are precursors to fastening elements (e.g., elongate ribs that are profile extruded and subsequently cut to form male fastening elements upon stretching in the direction of the ribs). Such ribs would not be able to engage loops before they are cut and stretched. Such ribs would also not be considered upstanding posts or discrete elements. Typically, male fastening elements that have loop-engaging heads have a maximum width dimension (in either dimension normal to the height) of up to about 1 (in some embodiments, 0.9, 0.8, 0.7, 0.6, 0.5, or 0.45) millimeter. In some embodiments, the male fastening elements have a maximum height (above the backing) of up to 3 mm, 1.5 mm, 1 mm, or 0.5 mm and, in some embodiments a minimum height of at least 0.03 mm, 0.05 mm, 0.1 mm, or 0.2 mm. In some embodiments, the upstanding posts have aspect ratio (that is, a ratio of height to width at the widest point) of at least about 0.25:1, 1:1, 2:1, 3:1, or 4:1.

Stretching in the first direction and subsequently the second direction can be carried out using a variety of methods. Stretching in the machine direction of a continuous web of indefinite length, monoaxial spreading in the machine direction can be performed by propelling the web over rolls of increasing speed, with the downweb roll speed faster than the upweb roll speed. In some embodiments, the first direction is the machine direction. Stretching in a cross-machine direction can be carried out on a continuous web using, for example, diverging rails, diverging disks, a series of bowed rollers, or a crown surface. Methods using diverging disks or a crown surface described, for example, in U.S. Ser. No. 61/647,833 and U.S. Ser. No. 61/647,862, each filed on May 16, 2012, may be useful for cross-direction stretching of the thermoplastic backing in the method according to the present disclosure. In some embodiments, the first direction is either the machine direction or cross-direction, and the discrete elements are positioned in a staggered array when viewed in the machine direction or cross-direction, respectively.

In some embodiments, laminating the thermoplastic backing to an extensible carrier is carried out after stretching in the first direction. The thermoplastic backing may be joined to a carrier, for example, by lamination (e.g., using thermal bonding or adhesives such as pressure sensitive adhesives), or other bonding methods (e.g., ultrasonic bonding, compression bonding, or surface bonding). The thermoplastic backing and the extensible carrier may be substantially continuously bonded or intermittently bonded. "Substantially continuously bonded" refers to being bonded without interruption in space or pattern. Substantially continuously bonded laminates can be formed by passing the thermoplastic backing and the extensible carrier between a heated smooth surfaced roll nip if at least one of them is thermally bondable or applying a substantially continuous adhesive coating or spray to one of the thermoplastic backing or extensible carrier before bringing it in contact with the other of the thermoplastic backing or extensible carrier. "Intermittently bonded" can mean not continuously bonded and refers to the thermoplastic backing and extensible carrier being bonded to one another at discrete spaced apart points or being substantially unbonded to one another in discrete, spaced apart areas. Intermittently bonded laminates can be formed, for example, by ultrasonic point bonding, by passing the thermoplastic backing and the extensible carrier through a heated patterned embossing roll nip if at least one of them is thermally bondable, or by applying discrete, spaced apart areas of adhesive to one of the thermoplastic backing or extensible carrier before bringing it into contact with the other of the thermoplastic backing or extensible carrier. An intermittently bonded laminate can also be made by feeding an adhesively coated apertured ply or scrim between the thermoplastic backing and the extensible carrier.

In some embodiments, the thermoplastic backing of the reticulated film disclosed herein can be joined to a fibrous carrier using surface bonding or loft-retaining bonding techniques. The term "surface-bonded" when referring to the bonding of fibrous materials means that parts of fiber surfaces of at least portions of fibers are melt-bonded to the second surface of the backing, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the thermoplastic backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the thermoplastic backing bonded thereto. In some of these embodiments, the joining comprises impinging heated gaseous fluid (e.g., ambient air, dehumidified air, nitrogen, an inert gas, or other gas mixture) onto a first surface of the fibrous web carrier while it is moving; impinging heated fluid onto the second surface of the thermoplastic backing while the continuous web is moving, wherein the second surface is opposite the discrete elements on the thermoplastic backing; and contacting the first surface of the fibrous web with the second surface of the thermoplastic backing so that the first surface of the fibrous web is melt-bonded (e.g., surface-bonded or bonded with a loft-retaining bond) to the second surface of the thermoplastic backing. Impinging heated gaseous fluid onto the first surface of the fibrous web and impinging heated gaseous fluid on the second surface of the backing may be carried out sequentially or simultaneously. Further methods and apparatus for joining a continuous web to a fibrous carrier web using heated gaseous fluid may be found in U.S. Pat. Appl. Pub. Nos. 2011/0151171 (Biegler et al.) and 2011/0147475 (Biegler et al.).

Referring again to FIG. 1C, the extensible carrier 30 may be continuous (i.e., without any through-penetrating holes) or discontinuous (e.g. comprising through-penetrating perforations or pores). The carrier may comprise a variety of suitable materials including woven webs, non-woven webs, textiles, plastic films (e.g., single- or multilayered films, coextruded films, laterally laminated films, or films comprising foam layers), and combinations thereof. The term "non-woven" refers to a material having a structure of individual fibers or threads that are interlaid but not in an identifiable manner such as in a knitted fabric. Examples of non-woven webs include spunbond webs, spunlaced webs, airlaid webs, meltblown web, and bonded carded webs. In some embodiments, including embodiments in which the laminate is a mechanical fastening laminate, the carrier is a fibrous material (e.g., a woven, nonwoven, or knit material). Useful fibrous materials may be made of natural fibers (e.g., wood or cotton fibers), synthetic fibers (e.g., thermoplastic fibers), or a combination of natural and synthetic fibers. Examples of suitable materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material. In some embodiments, the carrier 30 comprises multiple layers of nonwoven materials with, for example, at least one layer of a meltblown nonwoven and at least one layer of a spunbonded nonwoven, or any other suitable combination of nonwoven materials. For example, the carrier 30 may be a spunbond-meltbond-spunbond, spunbond-spunbond, or spunbond-spunbond-spunbond multilayer material. Or, the carrier 30 may be a composite web comprising a nonwoven layer and a dense film layer. A variety of combinations of film and nonwoven layers may be useful. Useful carriers 30 may have any suitable basis weight or thickness that is desired for a particular application. For a fibrous carrier, the basis weight may range, e.g., from at least about 5, 8, 10, 20, 30, or 40 grams per square meter, up to about 400, 200, or 100 grams per square meter. The carrier 30 may be up to about 5 mm, about 2 mm, or about 1 mm in thickness and/or at least about 0.1, about 0.2, or about 0.5 mm in thickness.

In some embodiments of the laminates according to the present disclosure or made by a method according to the present disclosure, the carrier 30 is elastic. In these embodiments, the carrier may be a film or fibrous. Examples of polymers for making elastic films or fibrous carriers include thermoplastic elastomers such as ABA block copolymers, polyurethane elastomers, polyolefin elastomers (e.g., metallocene polyolefin elastomers), olefin block copolymers, polyamide elastomers, ethylene vinyl acetate elastomers, and polyester elastomers. An ABA block copolymer elastomer generally is one where the A blocks are polystyrenic, and the B blocks are prepared from conjugated dienes (e.g., lower alkylene dienes). The A block is generally formed predominantly of substituted (e.g., alkylated) or unsubstituted styrenic moieties (e.g., polystyrene, poly(alphamethylstyrene), or poly(t-butylstyrene)), having an average molecular weight from about 4,000 to 50,000 grams per mole. The B block(s) is generally formed predominantly of conjugated dienes (e.g., isoprene, 1,3-butadiene, or ethylene-butylene monomers), which may be substituted or unsubstituted, and has an average molecular weight from about 5,000 to 500,000 grams per mole. The A and B blocks may be configured, for example, in linear, radial, or star configurations. An ABA block copolymer may contain multiple A and/or B blocks, which blocks may be made from the same or different monomers. A typical block copolymer is a linear ABA block copolymer, where the A blocks may be the same or different, or a block copolymer having more than three blocks, predominantly terminating with A blocks. Multi-block copolymers may contain, for example, a certain proportion of AB diblock copolymer, which tends to form a more tacky elastomeric film segment. Other elastic polymers can be blended with block copolymer elastomers, and various elastic polymers may be blended to have varying degrees of elastic properties.

Many types of thermoplastic elastomers are commercially available, including those from BASF, Florham Park, N.J., under the trade designation "STYROFLEX", from Kraton Polymers, Houston, Tex., under the trade designation "KRATON", from Dow Chemical, Midland, Mich., under the trade designation "PELLETHANE", "INFUSE", VERSIFY", or "NORDEL", from DSM, Heerlen, Netherlands, under the trade designation "ARNITEL", from E. I. duPont de Nemours and Company, Wilmington, Del., under the trade designation "HYTREL", from ExxonMobil, Irving, Tex. under the trade designation "VISTAMAXX", and more.

An elastic film may have a single layer of an elastomer, or the carrier may have a core made with an elastomer and at least one skin layer from a relatively non-elastic polymer, such as any of those described above for the thermoplastic backing. The materials and thicknesses of the multi-layer elastic carrier may be selected such that when the carrier is extended to a certain degree, the skin layers undergo plastic deformation. When the elastic layer recovers, the relatively non-elastic skin layer forms a textured surface on the elastic core. Such elastic films are described, for example, in U.S. Pat. No. 5,691,034 (Krueger et al.).

Referring again to FIG. 1D, when the carrier 30 in the laminate according to the present disclosure or made according to the method of the present disclosure is elastic, the openings 22 are retractable. As used herein, the term "retractable" can be understood to mean that a stretching force in the second direction can increase the width of the openings in the second direction, and release of the stretching force can at least partially close the plurality of openings to decrease the width of the openings in the second direction. Alternatively or additionally, the term "retractable", can be understood to mean that the thermoplastic backing is not macroscopically plastically deformed in the second direction. As such, it does not buckle when the stretching force is released. A reticulated film in which the openings are made by plastic deformation of the film in a particular direction by definition does not retract in that direction. Alternatively or additionally, the term "retractable" can be understood to mean that the openings in the reticulated film are not formed by molding or hole-punching. It is understood by a person skilled in the art that an opening that is molded or punched into a reticulated film is fixed in dimension by the molding or hole-punching process, and the lack of material in the opening is not recoverable. The retractable openings in the embodiment of the laminate disclosed herein in which the carrier is elastic are therefore distinguished from laminates of films that include openings formed by molding or plastic deformation. Even if the elastic were stretched upon laminating it to such a film, release of the stretching would result in buckling of the film between openings.

In some embodiments, the carrier 30 is extensible but non-elastic. In other words, the carrier may have an elongation of at least 25, 30, 40, or 50 percent but substantially no recovery from the elongation (e.g., up to 10 or 5 percent recovery). Suitable extensible carriers may include nonwovens (e.g., spunbond, spunbond meltblown spunbond, or carded nonwovens). Thus, in these embodiments, typically the extensible carrier is deformed upon stretching in the second direction. In some embodiments, the nonwoven may be a high elongation carded nonwoven (e.g., HEC). Other extensible, non-elastic carriers include thermoplastic films, including those made from any of the materials described above for the thermoplastic backing. The extensible, non-elastic film may be thinner than the thermoplastic backing in some embodiments. In any of the embodiments in which the carrier 30 is extensible but non-elastic, stretching the laminate in the second direction generally both forms a tear in the thermoplastic backing between two of the discrete elements and maintains the openings in an open configuration. However, the reticulated film itself may still have retractable openings. This can be determined by removing the reticulated film from the laminate, for example, peeling apart the carrier and the reticulated film. In some cases, removing the reticulated film from the laminate can be facilitated by submerging the laminate in liquid nitrogen.

The reticulated films according to the present disclosure that are removed from the carrier, for example, typically can also recover to at least to some extent from a deformation in the second direction. After the openings are formed, the openings provide regions in the reticulated film where means for transmission of force in the second direction is substantially absent. However, the locations where the thermoplastic backing is joined together can still develop stress in the second direction when the reticulated film is strained in the second direction. The balance of the openings and the locations where the thermoplastic backing is joined together provides the reticulated film with elastic behavior, even though the thermoplastic itself is typically not an elastomer. Thus, there is a tendency for the reticulated film to retract after being extended in the second direction if the thermoplastic backing is not plastically deformed upon stretching in the second direction. This retraction can be amplified by applying tension in the first direction. This recovery from stretching would not be possible for reticulated films that are plastically deformed (providing stretch-induced molecular orientation) in the second direction. With respect to the stretched film shown in FIG. 1B, in some embodiments of the method according to the present disclosure, the reticulated film can recover at least 70 or 75 and up to about 80 to 85 percent of its elongation after stretching in 2D upon release of the stretching force and application of tension in 1D without plastically deforming the film in 1D.

Figure 5:
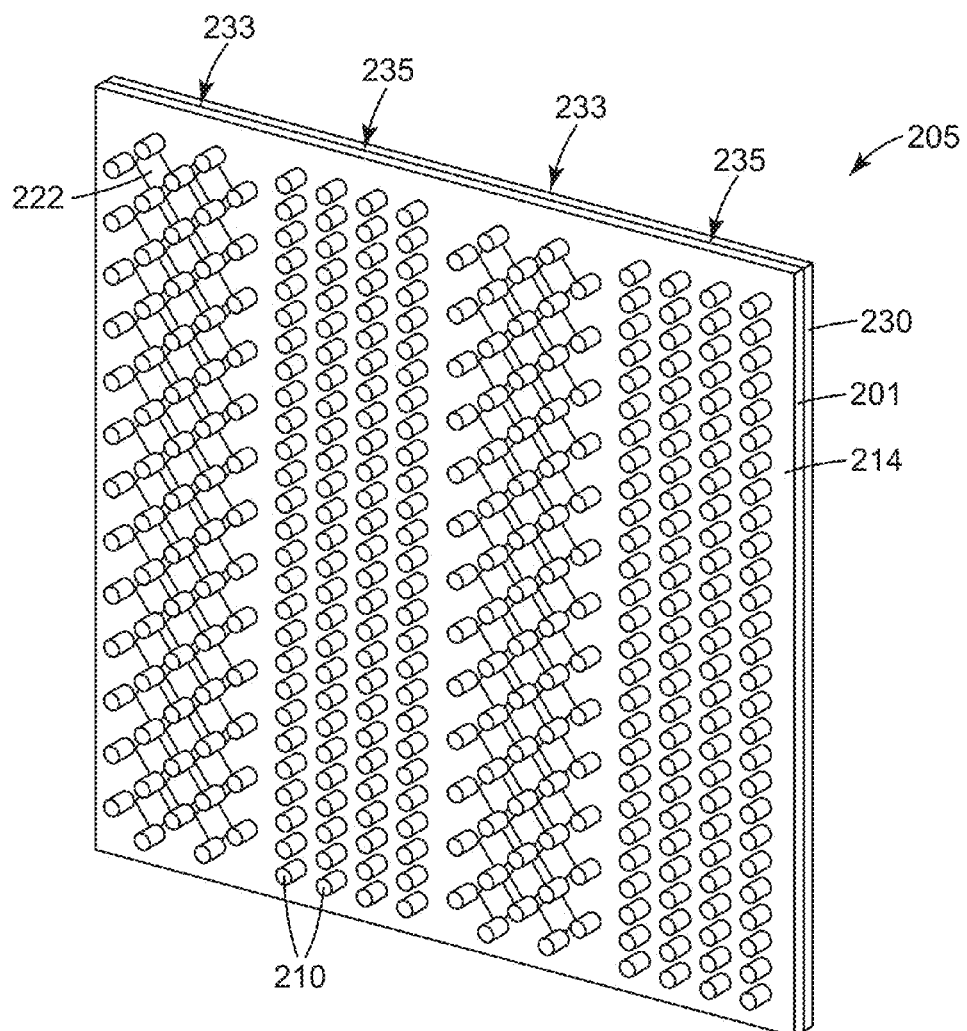
FIG. 5 is a perspective view of yet another embodiment of a laminate according to the present disclosure.

FIG. 5 illustrates another embodiment of the laminate 205 according to the present disclosure and/or made according to the method of the present disclosure. In laminate 205, the carrier 230 that is laminated to the partially reticulated film 201 comprises a first, extensible zone 233 and a second, inextensible zone 235. The first, extensible zone 233 underlies the openings 222, and the thermoplastic backing 214 overlying the second, inextensible zone 235 generally is not reticulated. In these embodiments, the reticulated film 201 can be considered partially reticulated. In embodiments of the method according to the present disclosure, in which the carrier comprises a first, extensible zone 233 and a second, inextensible zone 235, the tear between two adjacent discrete elements 210 is formed in the thermoplastic backing where it overlies the first, extensible zone 233, and tearing generally does not occur where the thermoplastic backing 214 overlies the second, inextensible zone 235. The film 201 is usually stretched in a first direction before lamination to the carrier 205, and the discrete elements 210, openings 222, and thermoplastic backing around the openings 214 can have any of the features described in any of the aforementioned embodiments. Carriers 230 having first, extensible and second, inextensible zones can be formed in a variety of ways as described below.

In some embodiments, carrier 230 is a film. Films comprising alternating first, extensible zones and second, inextensible zones useful for practicing the present disclosure can be made, for example, by side-by-side co-extrusion using any one of a number of useful methods. For example, U.S. Pat. No. 4,435,141 (Weisner et al.) describes a die with die bars for making a multi-component film having alternating segments in the film cross-direction. A die bar, or bars, at the exit region of the die segments two polymer flows using channels formed on the two outer faces of the die bar. The two sets of segmented polymer flows within these channels converge at a tip of the die bar where the two die bar faces meet. The segmented polymer flows are arranged so that when the two segmented polymer flows converge at the bar tip they form films that have alternating side-by-side zones of polymers. A similar process that further includes co-extruding a continuous outer skin layer on one or both outer faces of the side-by-side co-extruded film as described in U.S. Pat. No. 6,669,887 (Hilston et al.) may also be useful.

In some embodiments, management of the flow of different polymer compositions into side-by-side lanes to form a film such as carrier 230 can be carried out using a single manifold die with a distribution plate such as that described in, for example, in International Patent Application Publication No. WO 2011/097436 (Gorman et al.), incorporated by reference herein in its entirety. In some of these embodiments, the die comprises a first die cavity in a first die portion, a second die cavity in a second die portion, a distribution plate interposed between at least a portion (e.g., most or all) of the first die cavity and at least a portion (e.g., most or all) of the second die cavity. The distribution plate has a first side forming a boundary of the first die cavity, a second side forming a boundary of the second die cavity, a dispensing edge, a plurality of first extrusion channels, and a plurality of second extrusion channels. The first extrusion channels extend from entrance openings at the first die cavity to exit openings on the dispensing edge, and the second extrusion channels extend from entrance openings at the second die cavity to exit openings on the dispensing edge. The exit openings of the first extrusion channels and the exit openings of the second extrusion channels are disposed in alternating positions along the dispensing edge. Each of the first extrusion channels comprises two opposite side walls and a joining surface connecting the two opposite side walls, and the joining surface of at least some of the first extrusion channels is typically substantially parallel to the first side of the distribution plate.

Films comprising alternating first, extensible zones and second, inextensible zones useful for practicing the present disclosure such as carrier 230 shown in FIG. 5 can also be made by other extrusion dies that comprise a plurality of shims and have two cavities for molten polymer, such as those dies described, for example, in Int. Pat. App. Pub. No. WO 2011/119323 (Ausen et al.), incorporated herein by reference in its entirety. The plurality of shims positioned adjacent to one another together define first cavity, a second cavity, and a die slot, wherein the die slot has a distal opening wherein each of the plurality of shims defines a portion of the distal opening. At least a first one of the shims provides a passageway between the first cavity and the die slot, and at least a second one of the shims provides a passageway between the second cavity and the die slot. Typically, at least one of the shims is a spacer shim providing no conduit between either the first or the second cavity and the die slot.

Other side-by-side coextrusion techniques that may be useful for providing a film such as carrier 230 shown in FIG. 5 include those described in U.S. Pat. No. 6,159,544 (Liu et al.) and U.S. Pat. No. 7,678,316 (Ausen et al.) and Int. Pat. App. Pub. No. WO 2011/119323 (Ausen et al.).

Films comprising alternating first, extensible zones and second, inextensible zones useful for practicing the present disclosure include films wherein the second, inextensible zones are made from a relatively non-elastic polymeric composition, and wherein the first, extensible zones comprise strands of an elastic polymeric composition embedded in a matrix of the relatively non-elastic polymeric composition, in which the matrix is continuous with the second, inextensible zones. To make such films an elastic polymer melt stream can be segmented into multiple substreams and then extruded into the center of a melt stream of the relatively non-elastic polymeric composition, which is then formed into a film. This co-extrusion method creates a film that has multiple segmented flows within a matrix of another polymer. Dies useful for making films of this type include inclusion co-extrusion dies (e.g., those shown in U.S. Pat. No. 6,767,492 (Norquist et al.) and U.S. Pat. No. 5,429,856 (Krueger et al.)) and other similar apparatuses.

Carriers comprising alternating first, extensible zones and second, inextensible zones useful for practicing the present disclosure can also be multi-layer films of an elastomeric layer and at least one relatively non-elastic layer arranged in the film's thickness direction. Certain zones can be subjected to high heat and high pressure sufficient to create non-stretchable zones in the multi-layer film. In some embodiments, a coextruded multi-layer film can be stretched in a cross-machine direction to plastically deform the relatively non-elastic layer, and the stretched film can be passed over a patterned heat roll (e.g., in a range from 65° C. to 85° C.) to form parallel non-elastic zones in the machine direction. Delamination of the non-elastic layer in the elastic zones can be carried out, if desired, by cyclic heating and stretching and/or including additives in the non-elastic or elastic layers that promote delamination. In these embodiments, the elastic zones can have unencumbered retraction when a stretching force is released. The non-elastic layer can have a corrugated appearance when the film is in a relaxed state. In some of these embodiments, the carrier can be multi-layer such as that described in U.S. Pat. No. 5,376,430 (Swenson et al.), for example.

Carriers comprising alternating first, extensible zones and second, inextensible zones useful for practicing the present disclosure can also be made by mechanical activation. Mechanical activation processes include stretching with diverging disks or incremental stretching methods such as ring-rolling, structural elastic film processing (SELFing), which may be differential or profiled, in which not all material is strained in the direction of stretching, and other means of incrementally stretching webs as known in the art. The mechanically activated carrier may include films, fibrous layers, or combinations thereof. Mechanical activation generally uses intermeshing surfaces having alternating peaks and valleys. In ring-rolling, corrugated rolls provide the intermeshing surfaces through which the carrier is passed. The peaks can be defined as the apexes of outward pointing ridges of the corrugated rolls when such apparatuses are used. In other embodiments, the intermeshing surfaces are intermeshing discs, which may be mounted, for example, at spaced apart locations along a shaft as shown, for example, in U.S. Pat. No. 4,087,226 (Mercer). The intermeshing surfaces can also include rotating discs that intermesh with a stationary, grooved shoe. The peaks can also be defined as the peripheral surfaces (or center portion thereof) of the discs. In other incremental stretching apparatuses, the peaks of one of the intermeshing surfaces would be readily identifiable to a person skilled in the art.

An example of a suitable mechanical activation process is the ring-rolling process, described in U.S. Pat. No. 5,366,782 (Curro). Specifically, a ring-rolling apparatus includes opposing rolls having intermeshing teeth that incrementally stretch and thereby plastically deform the fibrous web or a portion thereof forming the outer cover, thereby rendering the outer cover stretchable in the ring-rolled regions. Activation performed in a single direction (for example the cross direction) yields an outer cover that is uniaxially stretchable. Activation performed in two directions (for example the machine and cross directions or any two other directions maintaining symmetry around the outer cover centerline) yields an outer cover that is biaxially stretchable.

In embodiments of the laminate or method according to the present disclosure in which the carrier has first, extensible zones and second, inextensible zones, the nature of the openings in the reticulated film that overly the extensible zones will be affected by the carrier as described above. Referring again to FIG. 5, when the extensible zones 233 of carrier 230 in laminate 200 are elastic, the openings 222 are retractable as described above. When the extensible zones 233 of carrier 230 in laminate 200 are non-elastic, extensible zones 233 typically maintain the openings 222 in an open configuration as described above.

Any of the machine direction and cross-direction methods described above can be useful for stretching the laminate in the second direction. Stretching the laminate, particularly in the second direction, may also be carried out by hand, for example. As described above, when stretching the laminate, stretching forces are exerted mainly on the extensible carrier. As a result, stretching a laminate in the second direction 2D can be carried out at least ten times faster than stretching the thermoplastic film itself. In some embodiments, stretching in the second direction can be carried out at a speed of at least up 15 centimeters per minute, at least 20 centimeters per minute, or at least 25 centimeters per minute. In some embodiments, stretching in the second direction can be carried out at a speed up to about 50 centimeters per minute or more.

In some embodiments of the method according to the present disclosure, laminating the thermoplastic backing to the carrier to provide the laminate is carried out before stretching the thermoplastic backing in the first direction. In these embodiments, in addition to each of the methods of joining the thermoplastic backing to the carrier described above (e.g., continuous or discontinuous thermal bonding, continuous or discontinuous adhesive bonding, ultrasonic bonding, compression bonding, or surface bonding) laminating the thermoplastic backing to the carrier can also be carried out by extrusion lamination. In some of these embodiments, the carrier is a fibrous carrier. For these embodiments, any of the machine direction and cross-direction stretching methods described above can be used sequentially for stretching in the first direction and subsequently the second direction in the method according to the present disclosure. A versatile stretching method that allows for monoaxial and sequential biaxial stretching of a thermoplastic web employs a flat film tenter apparatus. Such an apparatus grasps the thermoplastic web using a plurality of clips, grippers, or other film edge-grasping means along opposing edges of the thermoplastic web in such a way that monoaxial and biaxial stretching in the desired direction is obtained by propelling the grasping means at varying speeds along divergent rails. Increasing clip speed in the machine direction generally results in machine-direction stretching. Stretching at angles to the machine direction and cross-direction are also possible with a flat film tenter appararus. Monoaxial and biaxial stretching can also be accomplished, for example, by the methods and apparatus disclosed in U.S. Pat. No. 7,897,078 (Petersen et al.) and the references cited therein. Flat film tenter stretching apparatuses are commercially available, for example, from Brückner Maschinenbau GmbH, Siegsdorf, Germany.

In some embodiments, the method according to the present disclosure further comprises heating the thermoplastic backing. Heating may be useful, for example, before or during the stretching in the first direction. This may allow the thermoplastic backing to be more flexible for stretching. The temperature to which the thermoplastic backing is heated while stretching in the first direction may also affect the uniformity achieved when the backing is stretched in the second direction. In some embodiments in which the thermoplastic backing is a polypropylene backing, stretching in the first direction is carried out in a temperature range from 80° C. to 110° C., 85° C. to 100° C., or 90° C. to 95° C.

Figure 6A:
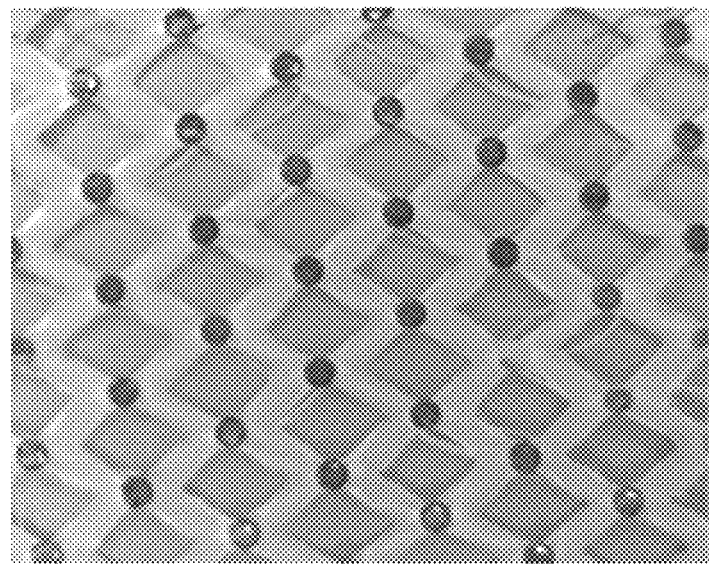
FIG. 6A is a picture of an embodiment of the reticulated film according to the present disclosure in which the thermoplastic backing was not heated while stretching in the second direction.
Figure 6B:
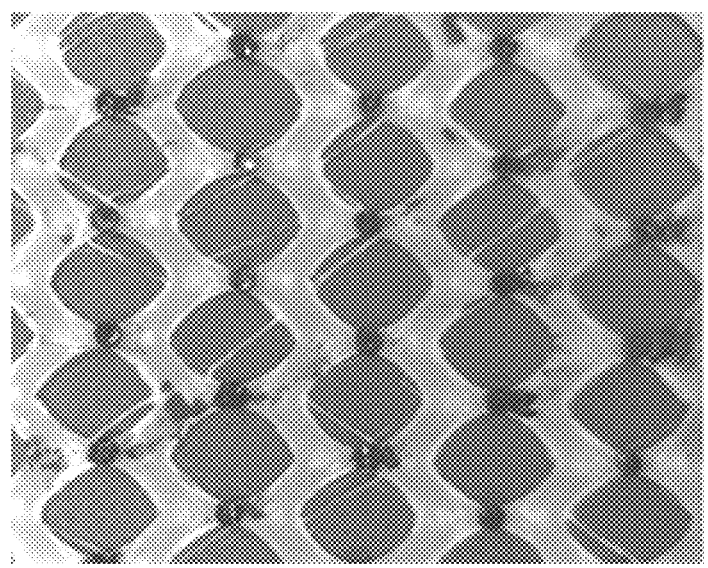
FIG. 6B is a picture of an embodiment of the reticulated film according to the present disclosure in which the thermoplastic backing was heated while stretching in the second direction.

Heating may also be useful, for example, before, during, or after stretching in the second direction. The force that is needed to tear and spread the film in the second direction decreases when the film is gently heated during this step. Also, the appearance of the reticulated film is changed when the film is heated while stretching in the second direction as shown in pictures shown in FIGS. 6A and 6B. FIG. 6A is a picture of an embodiment of the reticulated film according to the present disclosure in which the thermoplastic backing was not heated while stretching in the second direction. FIG. 6B is a picture of an embodiment of the reticulated film according to the present disclosure in which the same thermoplastic backing was heated to maintain a constant load while stretching in the second direction. The strand width in the reticulated film is typically larger when the backing is heated than when it is not heated. Also, the openings have sides that are more curved and corners that are more rounded when the backing is heated than when it is not heated. In some of these embodiments, the openings may have an approximately vesica piscis shape, which may also be considered an almond shape. Like the quadrilateral shape described above, the shape of the openings observed when the film is heated in the second direction still has two axis of symmetry, one in 1D and one in 2D. As can be observed in FIG. 6B, there are two discrete elements abutting opposite ends of any given opening (the more rounded extremes of the vesica piscis or almond shape), and there is one discrete element between the given opening and an adjacent opening aligned in the second direction (beyond the more pointed ends of the vesica piscis or almond shape).

In some embodiments, the laminate according to and/or made according to the present disclosure can be heated, for example, after stretching in the second direction. Heating at such a time may be useful for annealing the reticulated film, for example, to maintain the openings and to maintain the planarity of the thermoplastic backing, which may be useful, for example, if the reticulated film is to be removed from the carrier after the openings are formed and/or if the extensible carrier is elastic. In some embodiments, annealing comprises heating and then cooling (e.g., rapidly cooling) the laminate or reticulated film.

For any of these purposes, heating can be provided, for example, by IR irradiation, hot air treatment or by performing the stretching or annealing in a heat chamber. Rollers that may be used for stretching the thermoplastic backing in at least one of the first or second directions may be heated. Heated rollers may also be useful, for example, for annealing the reticulated film. For annealing, a continuous reticulated film can also be directed onto a chilled roller for rapid cooling. In some embodiments, heating is only applied to the second surface of the thermoplastic backing (i.e., the surface opposite the first surface from which the discrete elements protrude and the surface to which the carrier is joined) to minimize any damage to the discrete elements that may result from heating. For example, in these embodiments, only rollers that are in contact with the second surface of the thermoplastic backing or the carrier are heated. Heating is typically only carried out below the melting temperature of the thermoplastic backing.

Other web handling techniques may be useful for the laminate according to and/or made according to the method of the present disclosure after it is stretched in the second direction. For example, it may be useful to direct the reticulated film onto a high-friction roller or other high-friction surface to maintain the openings.

Figure 7A:
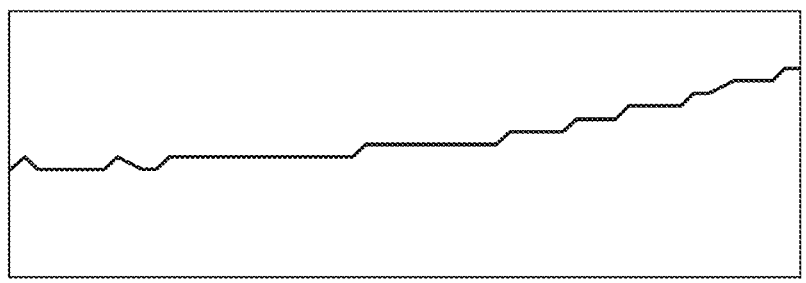
FIG. 7A is a portion of an extension versus load graph observed for Example 1.
Figure 7B:
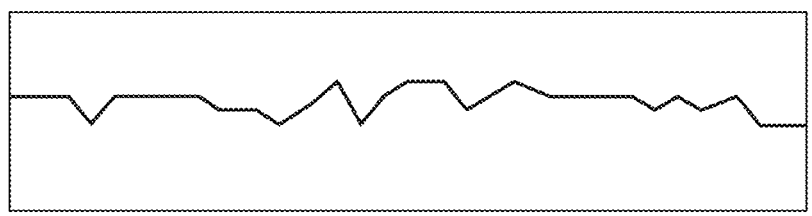
FIG. 7B is a portion of an extension versus load graph observed for the method of making a reticulated film, wherein the reticulated film is not joined to a carrier.

As described herein, laminating the thermoplastic backing to the extensible carrier before stretching in the second direction can be useful since some of the force of stretching is exerted on the extensible carrier. An illustration of the different mechanisms of stretching the thermoplastic backing, with and without a carrier, is shown in FIGS. 7A and 7B. A sample of a laminate similar to that shown in FIG. 1C was placed between the jaws of a tensile tester obtained from Instron, Norwood, Mass. The sample was stretched at a speed of 25.4 cm (10 inches) per minute to an extension of 5.08 cm (2 inches) in a load range from 3 to 6 lbf (13.3 N to 26.7 N). For comparison, a sample of a thermoplastic backing similar to that shown in FIG. 1B was stretched the same way. The sample was stretched at a speed of 2.54 cm (1 inch) per minute to 5.08 cm (1 inch per minute) to an extension of 4.19 cm (1.65 inches) with a load of about 2 lbf (8.9 N). The laminate can handle a higher load and be stretched at a faster rate. An expansion of the tensile extension vs. load curve for the non-laminated thermoplastic backing is shown in FIG. 7B. As shown in FIG. 7B, the load drops when the first tear forms, and a subsequent rise and drop of the load correspond to the formation of several tears in the reticulated film. In contrast, an expansion of the tensile extension vs. load curve for the laminate is shown in FIG. 7A. The load increases as each tear is formed, with a leveling in between. Since stresses can be handled by the carrier, the laminate can handle increasing load as the reticulated film is formed.

When the laminate according to the present disclosure is in the form of a continuous web, the laminate can be cut in the cross-machine direction, for example, to provide a patch of any desired size for a given application. When the discrete elements are male fastening elements, the patch can be considered a fastening patch or fastening laminate.

Fastening laminates made by the methods disclosed herein are useful, for example, in absorbent articles. Absorbent articles may have at least a front waist region, a rear waist region, and a longitudinal center line bisecting the front waist region and the rear waist region, wherein at least one of the front waist region or the rear waist region comprises the fastening laminate disclosed herein. The fastening laminate may be in the form of a fastening tab or landing zone that is bonded to at least one of the front waist region or the rear waist region. A fastening tab may extend outwardly from at least one of the left longitudinal edge or the right longitudinal edge of the absorbent article. In other embodiments, the fastening laminate may be an integral ear portion of the absorbent article. The carrier at the user's end of a fastening tab may exceed the extension of the mechanical fastening patch thereby providing a fingerlift. When the laminate disclosed herein is used in a fastening tab, exposed adhesive that may be present in some embodiments in at least some of the openings in the reticulated film may be useful for "anti-flagging" or for maintaining the disposable absorbent article in a rolled up state after use. The fastening laminate made by the methods disclosed herein may also be useful, for example, for disposable articles such as sanitary napkins. Mechanical fasteners and laminates made according to the present disclosure may also be useful in many other fastening applications, for example, assembly of automotive parts or any other application in which releasable attachment may be desirable.

Laminates according to the present disclosure and/or made according to the method of the present disclosure may also be useful as reflective surfaces for a variety of optical applications. For example, the discrete elements may be prisms (e.g., triangular, rectangular, rhombic, or hexagonal prisms), pyramids, or have a cross-section of a dodecahedral cross, any of which may be made according to the methods described above. A reticulated film as a prismatic reflective surface will tend to have a lower material cost than prismatic reflective surfaces made with a continuous film backing.

Reticulated thermoplastic films useful in the laminates according to the present disclosure and/or made according to the present disclosure are also described in U.S. Pat. App. Pub. No. 2014/0349062 (Chandrasekaran et al.), incorporated by reference herein in its entirety.

Some Embodiments of the Disclosure

In a first embodiment, the present disclosure provides a laminate comprising an at least partially reticulated thermoplastic film joined to an extensible carrier, the at least partially reticulated thermoplastic film comprising a thermoplastic backing comprising first and second major surfaces, a plurality of openings in the thermoplastic backing, and a plurality of discrete elements protruding from the first major surface of the thermoplastic backing, wherein there are two discrete elements abutting opposite ends of any given opening, wherein the two discrete elements are aligned in a first direction, wherein there is one discrete element between the given opening and an adjacent opening aligned in a second direction perpendicular to the first direction, wherein each portion of the thermoplastic backing around the given opening is plastically deformed in its lengthwise direction.

In a second embodiment, the present disclosure provides the laminate of the first embodiment, wherein at least some of the discrete elements each comprise one upstanding post.

In a third embodiment, the present disclosure provides the laminate of the first embodiment, wherein at least some of the discrete elements comprise more than one upstanding post on a surface protrusion.

In a fourth embodiment, the present disclosure provides the laminate of the second or third embodiment, wherein the upstanding post is part of a male fastening element.

In a fifth embodiment, the present disclosure provides the laminate of the fourth embodiment, wherein the male fastening element further comprises a cap distal from the thermoplastic backing.

In a sixth embodiment, the present disclosure provides the laminate of any one of the first to fifth embodiments, wherein the discrete elements protrude only from the first major surface of the thermoplastic backing.

In a seventh embodiment, the present disclosure provides the laminate of any one of the first to sixth embodiments, wherein the discrete elements have a height above the thermoplastic backing of at least 30 micrometers.

In an eighth embodiment, the present disclosure provides the laminate of any one of the first to seventh embodiments, wherein the thermoplastic backing is substantially uniform in thickness.

In a ninth embodiment, the present disclosure provides the laminate of any one of the first to eighth embodiments, wherein the thermoplastic backing is substantially planar.

In a tenth embodiment, the present disclosure provides the laminate of any one of the first to ninth embodiments, wherein at a point at an edge of the given opening, the thermoplastic backing has a higher stretch-induced molecular orientation than at a midpoint of the portion of the thermoplastic backing around the given opening.

In an eleventh embodiment, the present disclosure provides the laminate of any one of the first to tenth embodiments, wherein the plurality of discrete elements are arranged in a staggered array when viewed in the first direction.

In a twelfth embodiment, the present disclosure provides the laminate of any one of the first to eleventh embodiments, wherein the at least partially reticulated thermoplastic film is joined to the extensible carrier with adhesive.

In a thirteenth embodiment, the present disclosure provides the laminate of any one of the first to twelfth embodiments, wherein the extensible carrier is non-elastic.

In a fourteenth embodiment, the present disclosure provides the laminate of any one of the first to twelfth embodiments, wherein the extensible carrier is an elastic carrier, and wherein the given opening opens and closes upon extension and retraction of the elastic carrier.

In a fifteenth embodiment, the present disclosure provides the laminate of any one of the first to twelfth embodiments, wherein the first, extensible zone underlies the openings, and wherein the thermoplastic backing overlying the second, non-extensible zone is not reticulated.

In a sixteenth embodiment, the present disclosure provides an absorbent article comprising the laminate of any one of the first to fifteenth embodiments.

In a seventeenth embodiment, the present disclosure provides method of making the laminate of any one of the first to fifteenth embodiments, the method comprising:

providing a thermoplastic backing comprising first and second major surfaces and a plurality of discrete elements protruding from the first major surface of the thermoplastic backing, wherein the two discrete elements are aligned in a row in a first direction;

stretching the thermoplastic backing in the first direction to plastically deform the thermoplastic backing and separate the at least some of the discrete elements aligned in the row in the first direction, wherein the thermoplastic backing remains intact between the plurality of discrete elements after stretching it in the first direction;

laminating the thermoplastic backing to an extensible carrier to provide a laminate, wherein the extensible carrier is extensible in at least a second direction perpendicular to the first direction; and stretching the laminate in the second direction to form a tear in the thermoplastic backing between two adjacent of the discrete elements aligned in the row in the first direction, wherein the tear is interrupted by the two adjacent of the discrete elements, and wherein the tear provides the given opening. A plurality of the tears provides the plurality of openings.

In an eighteenth embodiment, the present disclosure provides the method of the seventeenth embodiment, wherein after stretching in the second direction, the thermoplastic backing has a thickness that is substantially the same as before stretching in the second direction.

In a nineteenth embodiment, the present disclosure provides the method of the seventeenth or eighteenth embodiment, wherein laminating the thermoplastic backing to the extensible carrier is carried out before stretching the thermoplastic backing in the first direction.

In a twentieth embodiment, the present disclosure provides the method of the seventeenth or eighteenth embodiment, wherein laminating the thermoplastic backing to the extensible carrier is carried out after stretching the thermoplastic backing in the first direction.

In a twenty-first embodiment, the present disclosure provides a method of making a laminate, the method comprising:

providing a thermoplastic backing comprising first and second major surfaces and a plurality of discrete elements protruding from the first major surface of the thermoplastic backing, wherein at least some of the discrete elements are aligned in a row in a first direction;

stretching the thermoplastic backing in the first direction to a degree sufficient to plastically deform the thermoplastic backing and separate the at least some of the discrete elements aligned in the row in the first direction, wherein the thermoplastic backing remains intact between the plurality of discrete elements after stretching it in the first direction;

laminating the thermoplastic backing to an extensible carrier to provide a laminate, wherein the extensible carrier is extensible in at least a second direction perpendicular to the first direction; and stretching the laminate in the second direction to form a tear in the thermoplastic backing between two adjacent of the discrete elements aligned in the row in the first direction, wherein the tear is interrupted by the two adjacent of the discrete elements.

In a twenty-second embodiment, the present disclosure provides the method of the twenty-first embodiment, wherein at least some of the discrete elements each comprise one upstanding post.

In a twenty-third embodiment, the present disclosure provides the method of the twenty-first embodiment, wherein at least some of the discrete elements comprise more than one upstanding post on a surface protrusion.

In a twenty-fourth embodiment, the present disclosure provides the method of the twenty-second or twenty-third embodiment, wherein the upstanding post is part of a male fastening element.

In a twenty-fifth embodiment, the present disclosure provides the method of the twenty-fourth embodiment, wherein the male fastening element further comprises a cap distal from the thermoplastic backing.

In a twenty-sixth embodiment, the present disclosure provides the method of any one of the twenty-first to twenty-fifth embodiments, wherein the discrete elements protrude only from the first major surface of the thermoplastic backing.

In a twenty-seventh embodiment, the present disclosure provides the method of any one of the twenty-first to twenty-sixth embodiments, wherein the discrete elements have a height above the thermoplastic backing of at least 30 micrometers.

In a twenty-eighth embodiment, the present disclosure provides the method of any one of the twenty-first to twenty-seventh embodiments, wherein the thermoplastic backing is substantially uniform in thickness.

In a twenty-ninth embodiment, the present disclosure provides the method of any one of the twenty-first to twenty-eighth embodiments, wherein the thermoplastic backing is substantially planar.

In a thirtieth embodiment, the present disclosure provides the method of any one of the twenty-first to twenty-ninth embodiments, wherein at a point at an edge of the given opening, the thermoplastic backing has a higher stretch-induced molecular orientation than at a midpoint of the portion of the thermoplastic backing around the given opening.

In a thirty-first embodiment, the present disclosure provides the method any one of the twenty-first to thirtieth embodiments, wherein the plurality of discrete elements are arranged in a staggered array when viewed in the first direction.

In a thirty-second embodiment, the present disclosure provides the method of any one of the twenty-first to thirty-first embodiments, wherein after stretching in the second direction, the thermoplastic backing has a thickness that is substantially the same as before stretching in the second direction.

In a thirty-third embodiment, the present disclosure provides the method of any one of the twenty-first to thirty-second embodiments, wherein laminating the thermoplastic backing to the extensible carrier is carried out before stretching the thermoplastic backing in the first direction.

In a thirty-fourth embodiment, the present disclosure provides the method of any one of the twenty-first to thirty-second embodiments, wherein laminating the thermoplastic backing to the extensible carrier is carried out after stretching the thermoplastic backing in the first direction.

In a thirty-fifth embodiment, the present disclosure provides the method of any one of the twenty-first to thirty-fourth embodiments, wherein the extensible carrier is elastic.

In a thirty-sixth embodiment, the present disclosure provides the method of any one of the twenty-first to thirty-fourth embodiments, wherein the extensible carrier is deformed upon stretching in the second direction.

In a thirty-seventh embodiment, the present disclosure provides the method of any one of the twenty-first to thirty-fourth embodiments, wherein the carrier comprises a first, extensible zone and a second, non-extensible zone, and wherein the tear is formed in the thermoplastic backing where it overlies the first, extensible zone.

In a thirty-eighth embodiment, the present disclosure provides the method of any one of the seventeenth to thirty-seventh embodiments, wherein laminating the thermoplastic backing to the extensible carrier comprises adhering the thermoplastic backing and the extensible carrier together.

In a thirty-ninth embodiment, the present disclosure provides the method of any one of the seventeenth to thirty-eighth embodiments, wherein a density of the discrete elements is in a range from 20 per $cm^2$ to 1000 per $cm^2$.

In a fortieth embodiment, the present disclosure provides the method of any one of the seventeenth to thirty-ninth embodiments, further comprising heating the thermoplastic backing while stretching it in the first direction.

In a forty-first embodiment, the present disclosure provides the method of any one of the seventeenth to fortieth embodiments, further comprising heating the thermoplastic backing while stretching it in the second direction.

In a forty-second embodiment, the present disclosure provides the method of any one of the seventeenth to forty-first embodiments, further comprising annealing the thermoplastic backing after stretching it in the second direction.

In a forty-third embodiment, the present disclosure provides the laminate of any one of the first to fifteenth embodiments, the absorbent article of the sixteenth embodiment, or the method of any one of the seventeenth to forty-second embodiments, wherein the plurality of openings have a diamond or almond shape.

In a forty-fourth embodiment, the present disclosure provides the laminate of any one of the first to fifteenth embodiments, the absorbent article of the sixteenth embodiment, or the method of any one of the seventeenth to forty-third embodiments, wherein the thermoplastic backing comprises at least one of polypropylene or polyethylene.

In order that this disclosure can be more fully understood, the following examples are set forth. It should be understood that these examples are for illustrative purposes only and are not to be construed as limiting this disclosure in any manner.

EXAMPLES

Illustrative Example 1

A thermoplastic backing with upstanding capped posts was prepared by feeding a stream of a film grade polypropylene copolymer, a polypropylene impact copolymer obtained from Dow Chemical Company, Midland, Mich., under the trade designation "DOW C700-35N POLYPROPYLENE RESIN" through a 2-inch (5.1-cm) single screw extruder. Barrel zones 1-7 were set at 176° C., 170° C., 180° C., 190° C., 200° C., 218° C., and 218° C., respectively. The molten resin was then fed through a sheet die to a rotating cylindrical mold. The temperature of the die was set at 216° C. (420° F.), and the temperature of cylindrical mold was set at 71° C. (160° F.). The screw speed was set at 80 rpm. The mold was water-cooled to provide rapid quenching that maintained the orientation in the polymer. The post density was 1600 posts per square inch (248 posts per square centimeter) arranged in a staggered array when viewed in the machine direction, and the post shape was conical. The cross-sectional shape of the post at the base was circular with a diameter of 350 micrometers. The line speed was set such that the film thickness was 100 micrometers. The web was fed into a cap forming apparatus after slitting it to the width to fit the apparatus. The posts were capped with oval shaped caps using the procedure described in U.S. Pat. No. 5,845,375 (Miller et al.). The caps were subsequently deformed using the procedure described in U.S. Pat. No. 6,132,660 (Kampfer) to provide "hook heads with downwardly projecting fiber engaging portions".

Stretching in the first direction was carried out by passing the web through two sets of rolls in which one roll was rotating faster that the other one. For each set of rolls, the bottom roll was a chrome roll, and the top roll was a rubber roll. For stretching, the temperature of each bottom chrome roll was set at 127° C. (260° F.) and that of each top rubber roll was set at 93° C. (200° F.). The draw ratio was 3.2 in the machine direction. A 3.8-cm (1.5-inch) wide sample was subsequently stretched in the cross direction in the jaws of a tensile tester obtained from Instron, Norwood, Mass., under the trade designation "INSTRON 5500R" with 2.54 cm gauge length. The sample was stretched at rate of 2.54 cm (1 inch)/minute to a final width of 7.6 cm (3 inches). A reticulated film such as that shown in FIGS. 1D and 2 was formed.

Illustrative Examples 2 to 7

Illustrative Examples 2 to 7 were made according to the methods of Illustrative Example 1, with the modification that various draw ratios were used for the machine direction stretching of various rolls. The draw ratios were varied from 1 to 4 in increments of 0.2. At draw ratios of 2.2 and less, stretching in the cross direction did not form a net but instead formed a biaxially stretched continuous film. After cross-direction stretching at 2.4 and higher, the film was reticulated.

The basis weight for each sample was measured before and after cross-direction stretching by punching out a 100-cm$^2$ sample from the reticulated film using a 25 cm by 4 cm punch. The sample was weighed on an electronic, analytical balance obtained from Mettler-Toledo International, Inc., Columbus, Ohio. The weight was multiplied by 100 to calculate the basis weight in grams per square meter (gsm).

The strand width of the reticulated film was measured by optical microscope obtained from Keyence Corporation of America, Elmwood Park, N.J., under the trade designation "VHX-100". Ten measurements were taken and averaged.

The draw ratio used for each Illustrative Example, the basis weight before and after cross-direction stretching, and the average strand width are shown in Table 1, below.

TABLE 1

| Illustrative Example | Draw Ratio | Basis Weight (gsm) before CD stretch | Basis Weight (gsm) after CD stretch | Strand Width (micrometers) |
|---|---|---|---|---|
| 1 | 3.2 | 60.1 | 41.8 | 400 |
| 2 | 2.4 | 71.8 | 49.4 | 482 |
| 3 | 2.6 | 68.8 | 47.5 | 460.7 |
| 4 | 2.8 | 66.2 | 46 | 442.3 |
| 5 | 3.0 | 62.0 | 44.2 | 411.1 |
| 6 | 3.4 | 58.2 | 40.2 | 398.7 |
| 7 | 3.8 | 52.8 | 39.2 | 363.2 |

A reticulated film made according to the method of Illustrative Example 1 was cut in the cross-direction across lines corresponding to "a" and "b" shown in FIG. 1D. Four small specimens were cut from the thermoplastic backing portions cut at line "a" and line "b". Each of the four specimens was dip-coated in epoxy. After curing for at least 24 hours, the epoxy-bound samples were microtomed to yield 10-μm-thick sections of epoxy and net that transected the net legs. The microtomed sections were placed on glass slides with 1.515 refractive index oil and covered with a cover slip. A DMRXE microscope (Leica Microsystems GmbH, Wetzlar, Germany) with a 10×/0.25 objective was equipped with an LC-POLSCOPE retardance imaging system (Lot-Oriel GmBH & Company, Darmstadt, Germany); a RETIGA EXI FAST 1394 digital color camera (QIMAGING, Surrey BC, Canada); and a 546.5 nm interference filter (Cambridge Research and Instrumentation, Inc., Hopkinton, Mass.). For each specimen, the imaging system was set to record the average retardance of a 7336-pixel imaging, an azimuth map, a horizontal line scan, and a false-color retardance map. Retardance is proportional to birefringence. The color photographs were converted to black and white. Areas of lighter color indicate areas of higher birefringence. Two of the photographs showed areas of higher birefringence at the edges (those corresponding to the right portion cut at line "a" and the left portion cut at line "b" in FIG. 1D. These are shown in FIGS. 3C and 3D. The other two photographs showed less difference across the thermoplastic backing portion.

Illustrative Examples 8 to 13

Illustrative Examples 8 to 13 were made according to the methods of Illustrative Example 1, with the modifications that the post density was 6000 posts per square inch (930 posts per square centimeter) and that various draw ratios were used for the machine direction stretching of various rolls as described in Illustrative Examples 2 to 7. The draw ratios were varied from 1 to 4 in increments of 0.2. At draw ratios of 3.0 and less, stretching in the cross direction did not form a net but instead formed a biaxially stretched continuous film. The basis weight for each sample was measured before cross-direction stretching using the method described in Illustrative Examples 2 to 7. After cross-direction stretching, the strand width of the reticulated film was measured by optical microscope using the method described in Illustrative Examples 2 to 7. The draw ratio used for each Illustrative Example, the basis weight before stretching, and the average strand width after cross-direction stretching are shown in Table 2, below.

TABLE 2

| Illustrative Example | Draw Ratio | Basis Weight (gsm) before CD stretch | Strand Width (micrometers) |
|---|---|---|---|
| 8 | 3.2 | 58.6 | 276.3 |
| 9 | 3.4 | 56.3 | 255.5 |
| 10 | 3.6 | 55.2 | 250.8 |

TABLE 2-continued

| Illustrative Example | Draw Ratio | Basis Weight (gsm) before CD stretch | Strand Width (micrometers) |
|---|---|---|---|
| 11 | 3.8 | 53.3 | 231.5 |
| 12 | 4.0 | 52.7 | 217.2 |
| 13 | 4.2 | 52.3 | 213.8 |

Illustrative Examples 14 to 21

Illustrative Examples 14 to 21 were made according to the methods of Illustrative Example 1, with the modifications that the thickness of the thermoplastic backing was either 70 micrometers or 130 micrometers. The thickness of the thermoplastic backing was altered by using the same mass of material extruded from the die but increasing the line speed. Various draw ratios were used for the machine direction stretching of various rolls as described in Illustrative Examples 2 to 7. The draw ratios were varied from 1 to 4 in increments of 0.2. At draw ratios of 1.8 and less for a 70-micrometer film and 2.6 and less for a 130-micrometer film, stretching in the cross direction did not form a net but instead formed a biaxially stretched continuous film. The basis weight for each sample was measured after cross-direction stretching using the method described in Illustrative Examples 2 to 7. After cross-direction stretching, the strand width of the reticulated film was measured by optical microscope using the method described in Illustrative Examples 2 to 7. The draw ratios and thermoplastic backing thickness used for each Illustrative Example, the basis weight after cross-direction stretching, and the average strand width after cross-direction stretching are shown in Table 3, below.

TABLE 3

| Illustrative Example | Thickness (micrometers) | Draw Ratio | Basis Weight (gsm) after CD stretch | Strand Width (micrometers) |
|---|---|---|---|---|
| 14 | 70 | 2.0 | 58.8 | 526.6 |
| 15 | 70 | 2.2 | 45.0 | 480.3 |
| 16 | 70 | 2.4 | 44.2 | 448.8 |
| 17 | 130 | 2.8 | 50.0 | 470.0 |
| 18 | 130 | 3.2 | 35.6 | 404.8 |
| 19 | 130 | 3.4 | 33.7 | 404.0 |
| 20 | 130 | 3.6 | 32.0 | 388.5 |
| 21 | 130 | 4 | 31.1 | 367.2 |

Illustrative Examples 22 to 27

Illustrative Examples 22 to 27 were made according to the methods of Illustrative Example 1, with the modifications that a different mold was used so that the diameter of the post at the base was 250 micrometers. Various draw ratios were used for the machine direction stretching of various rolls as described in Illustrative Examples 2 to 7. The draw ratios were varied from 1 to 4 in increments of 0.2. At draw ratios of 2.8 and less, stretching in the cross direction did not form a net but instead formed a biaxially stretched continuous film. The basis weight for each sample was measured before cross-direction stretching using the method described in Illustrative Examples 2 to 7. After cross-direction stretching, the strand width of the reticulated film was measured by optical microscope using the method described in Illustrative Examples 2 to 7. The draw ratios used for each Illustrative Example, the basis weight before cross-direction stretching, and the average strand width after cross-direction stretching are shown in Table 4, below.

TABLE 4

| Illustrative Example | Draw Ratio | Basis Weight (gsm) before CD stretch | Strand Width (micrometers) |
|---|---|---|---|
| 22 | 3.0 | 56.5 | 451.2 |
| 23 | 3.2 | 54.5 | 423.8 |
| 24 | 3.4 | 52.9 | 419.8 |
| 25 | 3.6 | 52.1 | 410.3 |
| 26 | 3.8 | 51.8 | 396.6 |
| 27 | 4.0 | 48.4 | 371.6 |

Illustrative Examples 28 to 39

Illustrative Examples 28 to 39 were made according to the methods of Illustrative Example 1, with the modification that high density polyethylene (H6030) (PE) obtained from LyondellBasell Industries, Houston, Tex., was used instead of polypropylene (PP). Various draw ratios were used for the machine direction stretching of various rolls as described in Illustrative Examples 2 to 7 except the draw ratios were varied from 3 to 4 in increments of 0.2. The basis weight for each sample was measured before cross-direction stretching using the method described in Illustrative Examples 2 to 7. After cross-direction stretching, the strand width of the reticulated film was measured by optical microscope using the method described in Illustrative Examples 2 to 7. The draw ratios and thermoplastic used for each Illustrative Example, the basis weight before cross-direction stretching, and the average strand width after cross-direction stretching are shown in Table 5, below.

TABLE 5

| Illustrative Example | Thermoplastic | Draw Ratio | Basis Weight (gsm) before CD stretch | Strand Width (micrometers) |
|---|---|---|---|---|
| 28 | PE | 3 | 66.5 | 467.3 |
| 29 | PE | 3.2 | 62.6 | 454.8 |
| 30 | PE | 3.4 | 56.7 | 449.2 |
| 31 | PE | 3.6 | 54.4 | 437.6 |
| 32 | PE | 3.8 | 51.5 | 417.8 |
| 33 | PE | 4 | 51.2 | 409.5 |
| 34 | PP | 3 | 56.5 | 451.1 |
| 35 | PP | 3.2 | 54.5 | 423.8 |
| 36 | PP | 3.4 | 52.9 | 419.8 |
| 37 | PP | 3.6 | 52.1 | 410.3 |
| 38 | PP | 3.8 | 51.8 | 396.6 |
| 39 | PP | 4 | 48.4 | 371.6 |

Illustrative Example 40

Illustrative Example 40 was prepared from a film extruded, molded with posts that were subsequently capped, and stretched in the machine direction according to the method of Illustrative Example 1. Two different punches were used to punch four samples from the film. The two punches were 37 mm by 25 mm and 30 mm by 20 mm, respectively. Two samples were prepared from the first punch with the 37-mm edges aligned in the machine direction, and one sample was prepared from the first punch with the 37-mm edges aligned in the cross-machine direction. One sample was prepared from the second punch with its 30-mm edges aligned in the machine direction. Each sample was stretched by hand in the cross-direction to two times its width, and a reticulated film was formed. The length and width of each sample were measured. Next each sample was pulled by hand in the machine direction to place some tension on the film. The length and width of each sample were measured again. The original length (L) and width (W) of each sample, the length and width of each sample after stretching in the width direction to make the reticulated film, and the length and width of each sample after tension was applied on the reticulated film in the machine direction are shown in Table 6, below.

photograph was converted to grayscale and is shown in FIG. 3B. Areas of lighter color, which are on the edges of the thermoplastic backing portions around the openings, indicate areas of higher birefringence. Although not visible in the gray scale image of FIG. 3B, the highest birefringence appeared orange and was located in the thermoplastic backing on the edge of the opening near the location of the discrete element.

TABLE 6

| Original (1) | | Stretched (2) | | Stretched/Original | | Tensioned (3) | | Tensioned/Original | |
|---|---|---|---|---|---|---|---|---|---|
| L (mm) | W (mm) | L (mm) | W (mm) | L2/L1 | W2/W1 | L (mm) | W (mm) | L3/L1 | W3/W1 |
| 37 | 25 | 27 | 50 | 0.73 | 2 | 36 | 31 | 0.97 | 1.24 |
| 37 | 25 | 28 | 50 | 0.76 | 2 | 37 | 30 | 1.00 | 1.20 |
| 25 | 37 | 20 | 74 | 0.80 | 2 | 23 | 45 | 0.92 | 1.22 |
| 30 | 20 | 25 | 39 | 0.83 | 1.95 | 29 | 24 | 0.97 | 1.20 |

The recovery from stretching can be calculated from the equation $(W2 - W1) - (W3 - W1)/(W2 - W1)$. The percent recoveries for the samples were 76%, 80%, 78%, and 79%, respectively.

Illustrative Example 41

Illustrative Example 41 was prepared from a film extruded, molded with posts that were subsequently capped, and stretched in the machine direction according to the method of Illustrative Example 1. A piece 2.54 cm long and 12.5 cm wide was cut from the film and placed between the jaws of a tensile tester obtained from Instron, Norwood, Mass., under the trade designation "INSTRON 5500R" with 2.54 cm gauge length. The sample was stretched at a speed of about 2.54 cm (1 inch) per minute to a length of 13.5 cm. A heat gun was used to intermittently heat the sample to keep the load on the sample approximately constant at 6 pounds (8.9 N). A picture of the reticulated film was taken with the optical microscope obtained from Keyence Corporation of America under the trade designation "VHX-100" and in shown in FIG. 6B. For comparison, a sample stretched at room temperature as in Illustrative Example 1 is shown in FIG. 6A.

Illustrative Example 42

Illustrative Example 42 was prepared from a film extruded, molded with posts that were subsequently capped, and stretched in the machine direction according to the method of Illustrative Example 1. A 2 cm by 2 cm sample of the film was examined with a polarization microscope "LEICA DM2700P", obtained from Microsystems GmbH, Wetzlar, Germany. The microscope was equipped with cross polars and was used in transmission mode. The polarizer and analyzer were placed at 90 degrees to each other for dark field imaging. The sample was placed between the polarizer and analyzer, and a 50× image was recorded using a digital microscope camera "PROGRES C3", obtained from Jenoptik Optical Systems, GmbH, Jena, Germany, with the focus on the thermoplastic backing. The color photograph was converted to grayscale and is shown in FIG. 3A. In the color image, the areas with highest birefringence appeared orange, and in the grayscale photograph shown in FIG. 3A, these areas appear as the darker, triangular areas above and below the round upstanding elements reveals. The sample was then stretched by hand in the cross-machine direction to form a reticulated film, and the sample was imaged using the polarization microscope under the same conditions as the sample before stretching in the second direction. The color For comparison, a portion of a film obtained from DelStar Technologies, Inc., Middletown, Del., under the trade designation "DELNET X-550 NAT" was also imaged under the polarization microscope described above. The apertured film had a hexagonal shaped unit cell including six triangular shaped subcells. It is believed that the aperture film is made by the method described in U.S. Pat. No. 5,207,962 (Hovis et al.). The film portion corresponding to one side of each triangle had a higher birefringence than the other two, with the highest birefringence centered widthwise and lengthwise. For the film portions corresponding to the other two sides, the birefringence appeared substantially the same across the width of the film portions.

Example 1

Example 1 was prepared from a film extruded, molded with posts that were subsequently capped, and stretched in the machine direction according to the method of Illustrative Example 1. The film was laminated to an elastic carrier obtained from 3M Company, St. Paul, Minn., under the trade designation "3M WAIST ELASTIC B-430-W" using adhesive obtained from 3M Company under the trade designation "SUPER 77". A continuous spray coating of the adhesive was used to give a coating level of 5 grams per square meter. A piece 2.54 cm by 10 cm was cut from the laminate and placed between the jaws of a tensile tester obtained from Instron, Norwood, Mass., under the trade designation "INSTRON 5500R" with 2.54 cm gauge length. The sample was stretched at a speed of 25.4 cm (10 inches) per minute to an extension of 5.08 cm (2 inches) in a load range from 3 to 6 lbf (13.3 to 26.7 N). An expansion of the tensile extension vs. load curve is shown in FIG. 7A.

For comparison, a sample was prepared and stretched in the same manner as in Example 1 except not laminated to a carrier. The sample was stretched at a speed of 2.54 cm (1 inch) per minute to 5.08 cm (2 inches) per minute to an extension of 4.19 cm (1.65 inches) with a load of about 2 lbf (8.9 N). An expansion of the tensile extension vs. load curve is shown in FIG. 7B.

Example 2

Example 2 was prepared according to the method of Example 1, except that a portion of the film (5 cm by 10 cm)

was laminated to an elastic carrier obtained from 3M Company under the trade designation "3M FLUTED ELASTIC". The sample was then stretched by hand. Openings formed only over the stretchable portions of the elastic. The resulting laminate had an appearance similar to that shown in FIG. 5.

This disclosure is not limited to the above-described embodiments but is to be controlled by the limitations set forth in the following claims and any equivalents thereof. This disclosure may be suitably practiced in the absence of any element not specifically disclosed herein.

What is claimed is:

1. A laminate comprising an at least partially reticulated thermoplastic film joined to an extensible carrier, the at least partially reticulated thermoplastic film comprising:
   a thermoplastic backing comprising first and second major surfaces, a plurality of openings in the thermoplastic backing, and a plurality of discrete elements protruding from the first major surface of the thermoplastic backing, wherein there are two discrete elements abutting opposite ends of any given opening, wherein the two discrete elements are aligned in a first direction, wherein there is one discrete element between the given opening and an adjacent opening aligned in a second direction perpendicular to the first direction, wherein each portion of the thermoplastic backing around the given opening is plastically deformed in its lengthwise direction,
   wherein the carrier comprises a first, extensible zone and a second, non-extensible zone, wherein the first, extensible zone underlies the openings, and wherein the thermoplastic backing overlying the second, non-extensible zone is not reticulated.

2. The laminate of claim 1, wherein at least some of the discrete elements each comprise one upstanding post.

3. The laminate of claim 2, wherein the upstanding post is part of a male fastening element.

4. The laminate of claim 1, wherein at least some of the discrete elements comprise multiple upstanding posts on a surface protrusion.

5. The laminate of claim 1, wherein the discrete elements have a height above the thermoplastic backing of at least 30 micrometers.

6. The laminate of claim 1, wherein the thermoplastic backing is substantially planar.

7. The laminate of claim 1, wherein the plurality of discrete elements are arranged in a staggered array when viewed in the first direction.

8. The laminate of claim 1, wherein the thermoplastic backing comprises at least one of polyethylene or polypropylene.

9. The laminate of claim 1, wherein the at least partially reticulated thermoplastic film is bonded to the extensible carrier with adhesive.

10. The laminate of claim 1, wherein the extensible carrier is non-elastic.

11. The laminate of claim 1, wherein the extensible carrier is an elastic carrier, and wherein the given opening opens and closes upon extension and retraction of the elastic carrier.

12. A method of making the laminate of claim 1, the method comprising:
    providing a thermoplastic backing comprising first and second major surfaces and a plurality of discrete elements protruding from the first major surface of the thermoplastic backing, wherein at least some of the discrete elements are aligned in a row in a first direction;
    stretching the thermoplastic backing in the first direction to a degree sufficient to plastically deform the thermoplastic backing and separate the at least some of the discrete elements aligned in the row in the first direction, wherein the thermoplastic backing remains intact between the plurality of discrete elements after stretching it in the first direction;
    laminating the thermoplastic backing to an extensible carrier to provide a laminate, wherein the extensible carrier is extensible in at least a second direction perpendicular to the first direction; and
    stretching the laminate in the second direction to form a tear in the thermoplastic backing between two adjacent of the discrete elements aligned in the row in the first direction, wherein the tear is interrupted by the two adjacent of the discrete elements, wherein the carrier comprises a first, extensible zone and a second, non-extensible zone, and wherein the tear is formed in the thermoplastic backing where it overlies the first, extensible zone.

13. The method of claim 12, wherein the extensible carrier is elastic.

14. The method of claim 12, wherein the extensible carrier is deformed upon stretching in the second direction.

15. The method of claim 12, wherein after stretching in the second direction, the thermoplastic backing has a thickness that is substantially the same as before stretching in the second direction.

16. The method of claim 12, wherein laminating the thermoplastic backing to the extensible carrier is carried out before stretching the thermoplastic backing in the first direction.

17. The method of claim 12, wherein laminating the thermoplastic backing to the extensible carrier is carried out after stretching the thermoplastic backing in the first direction.

18. The method of claim 12, wherein laminating the thermoplastic backing to the extensible carrier comprises adhering the thermoplastic backing and the extensible carrier together.

* * * * *